(12) United States Patent  
Diethelm et al.

(10) Patent No.: US 10,441,576 B2  
(45) Date of Patent: *Oct. 15, 2019

(54) SUBSTITUTED 1,2-DIHYDRO-3H PYRROLO[1,2-C]IMIDAZOL-3 ONE ANTIBACTERIALS

(71) Applicant: IDORSIA PHARMACEUTICALS LTD., Allschwil (CH)

(72) Inventors: Stefan Diethelm, Allschwil (CH); Philippe Panchaud, Allschwil (CH); Georg Rueedi, Allschwil (CH); Jean-Luc Specklin, Allschwil (CH); Jean-Philippe Surivet, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/751,596

(22) PCT Filed: Aug. 10, 2016

(86) PCT No.: PCT/EP2016/069036  
§ 371 (c)(1),  
(2) Date: Feb. 9, 2018

(87) PCT Pub. No.: WO2017/025562  
PCT Pub. Date: Feb. 16, 2017

(65) Prior Publication Data  
US 2018/0235938 A1    Aug. 23, 2018

(30) Foreign Application Priority Data

Aug. 11, 2015  (WO) .................. PCT/EP2015/068450  
Sep. 2, 2015   (WO) .................. PCT/EP2015/070054

(51) Int. Cl.  
*A61K 31/4188*    (2006.01)  
*A61K 31/5377*    (2006.01)  
(Continued)

(52) U.S. Cl.  
CPC ...... *A61K 31/4188* (2013.01); *A61K 31/5377* (2013.01); *A61P 31/04* (2018.01); *C07D 487/04* (2013.01)

(58) Field of Classification Search  
CPC . A61K 31/4188; A61K 31/5377; A61P 31/04; C07D 487/04  
(Continued)

(56) References Cited

U.S. PATENT DOCUMENTS 9,624,206 B2   4/2017   Chapoux et al.  
9,796,686 B2   10/2017  Chapoux et al.  
(Continued)

FOREIGN PATENT DOCUMENTS

WO   WO 03/077914 A1   9/2003  
WO   WO 2005/036964 A1   4/2005  
(Continued)

OTHER PUBLICATIONS

"Methods for Dilution Antimicrobial Susceptibility Tests for Bacteria that Grow Aerobically", Approved standard, 7th ed., Clinical and Laboratory Standards Institute (CLSI) Document M7-A7, USA (2006), vol. 26(2) (64 pages total).

(Continued)

*Primary Examiner* — Brenda L Coleman  
(74) *Attorney, Agent, or Firm* — Arent Fox LLP

(57) ABSTRACT

The invention relates to antibacterial compounds of formula I

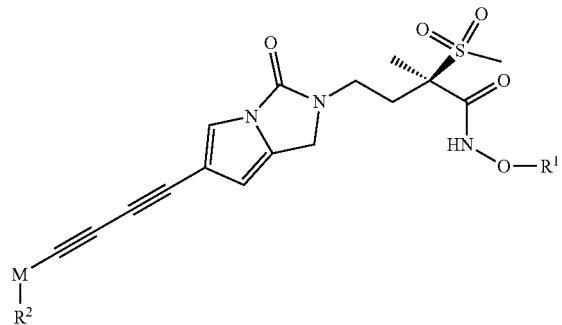

wherein M is one of the groups $M^A$, $M^B$ and $M^C$ represented below

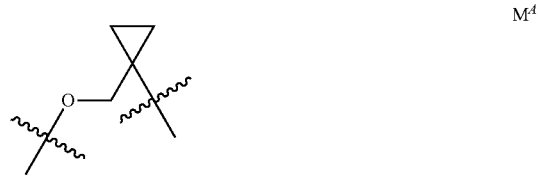

$M^A$

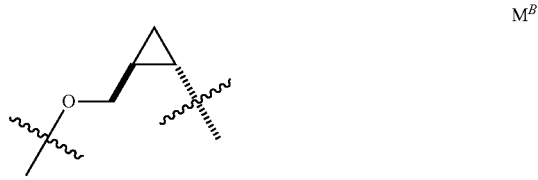

$M^B$

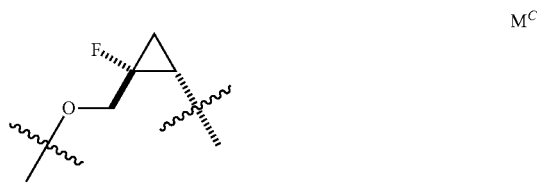

$M^C$ (Continued)

and either R¹ represents H and R² represents a cleavable group as defined in the claims or R² represents H and R¹ represents a cleavable group as defined in the claims; and salts thereof.

16 Claims, No Drawings

(51) Int. Cl.
  *C07D 487/04* (2006.01)
  *A61P 31/04* (2006.01)

(58) Field of Classification Search
  USPC .................................. 514/386; 548/302.7
  See application file for complete search history.

(56) References Cited

U.S. PATENT DOCUMENTS

| | | |
|---|---|---|
| 9,802,901 B2 | 10/2017 | Gauvin et al. |
| 2016/0221959 A1 | 8/2016 | Gauvin et al. |
| 2017/0029411 A1 | 2/2017 | Chapoux et al. |
| 2017/0081292 A1 | 3/2017 | Chapoux et al. |
| 2017/0107223 A1 | 4/2017 | Chapoux et al. |
| 2017/0355687 A1 | 12/2017 | Chapoux et al. |

FOREIGN PATENT DOCUMENTS

| | | |
|---|---|---|
| WO | WO 2010/032147 A2 | 3/2010 |
| WO | WO 2010/060785 A1 | 6/2010 |
| WO | WO 2011/045703 A2 | 4/2011 |
| WO | WO 2011/073845 A1 | 6/2011 |
| WO | WO 2012/120397 A1 | 9/2012 |
| WO | WO 2012/137094 A1 | 10/2012 |
| WO | WO 2012/137099 A1 | 10/2012 |
| WO | WO 2013/170165 A1 | 11/2013 |
| WO | WO 2015/036964 A1 | 3/2015 |
| WO | WO 2015/066413 A1 | 5/2015 |
| WO | WO 2015/091741 A1 | 6/2015 |
| WO | WO 2015/132228 A1 | 9/2015 |
| WO | WO 2015/173329 A1 | 11/2015 |
| WO | WO 2016/079688 A1 | 5/2016 |
| WO | WO 2017/036968 A1 | 3/2017 |
| WO | WO 2017/037039 A1 | 3/2017 |
| WO | WO 2017/037221 A1 | 3/2017 |
| WO | WO 2017/098440 A1 | 6/2017 |
| WO | WO 2017/198647 A1 | 11/2017 |

OTHER PUBLICATIONS

Benz, "Synthesis of Amides and Related Compounds in Comprehensive Organic Synthesis," 1991, vol. 6, 381-417.
Chodkiewicz et al., "Nouvelle Synthése de composes polyacétyléniques conjugués symétriques et dissymétriques," C.R. Hebd. Seances Acad. Sci., 1955, vol. 241, pp. 1055-1057 (8 pages total).
J. P. Sanford et al., "The Sanford Guide to Antimicrobial Therapy", 42nd Edition, Antimicrobial Therapy, Inc., 2012 (4 pages total).
Johan Wouters and Luc Quéré "Pharmaceutical Salts and Co-crystals," 2012 (10 pages total).
Marmer et al., "The Preparation and Reactions of Novel O-Acylhydroxylamines," J. Org. Chem. (1972), vol. 37, pp. 3520-3523.
Montgomery et al., "Pyridone Methylsulfone Hydroxamate LpxC Inhibitors for the Treatment of Serious Gram-Negative Infections," J. Med. Chem. (2012), 55(4), pp. 1662-1670.
R. C. Larock "Comprehensive Organic Transformations, A guide to Functional Group Preparations"; 2nd Edition (1999), Section Nitriles, Carboxylic Acids and Derivatives, p. 1941-1949.
Remington, The Science and Practice of Pharmacy, 21st Edition (2005), Part 5, "Pharmaceutical Manufacturing," (5 pages total).
Sakagami et al., "Synthesis, in vitro pharmacology, and pharmacokinetic profiles of 2-[1-amino-1-carboxy-2-(9H-xanthen-9-yl)-ethyl]-1-fluoro-cyclopropanecarboxylic acid and its 6-heptyl ester, a potent mGluR2 antagonist," Bioorg. Med. Chem. (2008), 16(8), pp. 4359-4366.
Sato et al., "One-pot reductive amination of aldehydes and ketones with alpha-picoline-borane in methanol, in water, and in neat conditions," Tetrahedron (2004), 60, pp. 7899-7906.
Sonogashira, "Cross-coupling Reactions to sp Carbon Atoms in Metal-Catalyzed Reactions," Diederich, F., Stang, P.J., Eds.; Wiley-VCH, New York (1998), pp. 203-229.
Stahl et al., "Handbook of Pharmaceutical Salts. Properties, Selection and Use" (2008), pp. 329-350.
T.W. Greene & P.G.M. Wuts, Protective Groups in Organic Synthesis, 3rd Ed. (1999), pp. 369-441 (Publisher: John Wiley and Sons, Inc., New York, N.Y.).
T.W. Greene and P.G.M. Wuts, Protective Groups in Organic Synthesis, 3rd Ed (1999), pp. 23-147.
T.W. Greene and P.G.M. Wuts, Protective Groups in Organic Synthesis, 3rd Ed. (1999), Wiley-Interscience (3 pages total).

SUBSTITUTED 1,2-DIHYDRO-3H PYRROLO[1,2-C]IMIDAZOL-3 ONE ANTIBACTERIALS

CROSS REFERENCE TO RELATED APPLICATIONS

This application is a 35 U.S.C. § 371 National Phase of PCT Application No. PCT/EP2016/069036 filed Aug. 10, 2016, which claims benefit to International Application Nos. PCT/EP2015/070054 filed Sep. 2, 2015 and PCT/EP2015/068450 filed Aug. 11, 2015, the disclosures of each of which are hereby incorporated by reference in their entirety.

The present invention concerns substituted antibacterial 1,2-dihydro-3H-pyrrolo[1,2-c]imidazol-3-one derivatives, pharmaceutical compositions containing them and uses of these compounds in the manufacture of medicaments for the treatment of bacterial infections. These compounds are useful antimicrobial agents effective against a variety of human and veterinary pathogens, especially Gram negative aerobic and anaerobic bacteria. The compounds of the present invention can optionally be employed in combination, either sequentially or simultaneously, with one or more therapeutic agents effective against bacterial infections.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., Enterobacteriaceae such as *Klebsiella pneumoniae, Acinetobacter baumannii* and *Pseudomonas aeruginosa*, major sources of infections, are becoming multi-drug resistant and therefore difficult if not impossible to treat. This is particularly the case for Gram-negative organisms where the situation is getting worrisome since no novel agents have been approved for decades and the development pipeline looks empty.

Therefore, there is an important medical need for new antibacterial compounds addressing Gram-negative resistant bacteria, in particular third generation cephalosporins- and carbapenem-resistant *Klebsiella pneumoniae* and multi-drug-resistant *Pseudomonas aeruginosa* and *Acinetobacter baumannii*. One way to tackle the problem of cross resistance to established classes of antibiotics is to inhibit a new essential target. In this respect, LpxC, which is an enzyme in the biosynthesis of lipopolysaccharides (a major constituent of the outer membrane of Gram-negative bacteria), has received some attention and several patent applications relating to LpxC inhibitors have been published recently.

For example, WO 2011/045703, WO 2011/073845, WO 2012/120397, WO 2012/137094, WO 2012/137099, WO 2013/170165 and WO 2015/066413 describe antibacterial compounds having a N-hydroxy-2-methyl-2-(methylsulfonyl)butanamide side chain bound to a monocyclic aromatic or heteroaromatic ring system.

Furthermore WO 2013/170165 describes notably antibacterial compounds of formula (A0)

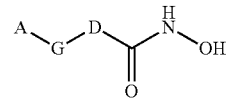

(A0)

wherein A is a substituted alkyl group, wherein at least one substituent is hydroxy, or A is a substituted cycloalkyl group, wherein at least one substituent is hydroxy or hydroxyalkyl; G is a group comprising at least one carbon-carbon double or triple bond and/or a phenyl ring; D represents a group selected from

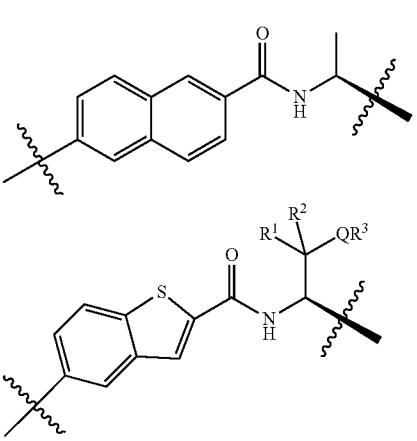

Q is O or NR, wherein R is H or an unsubstituted $(C_1-C_3)$ alkyl; $R^1$ and $R^2$ independently are selected from the group consisting of H and substituted or unsubstituted $(C_1-C_3)$ alkyl, or $R^1$ and $R^2$, together with the carbon atom to which they are attached, form an unsubstituted $(C_3-C_4)$cycloalkyl group or an unsubstituted 4-6 membered heterocyclic group; and $R^3$ is selected from the group consisting of hydrogen, substituted or unsubstituted $(C_1-C_3)$alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclyl, substituted or unsubstituted heterocyclylalkyl, substituted or unsubstituted heteroaryl, and substituted or unsubstituted heteroarylalkyl.

In WO 2015/036964, we have reported antibacterial 2H-indazole derivatives of general formula (A2)

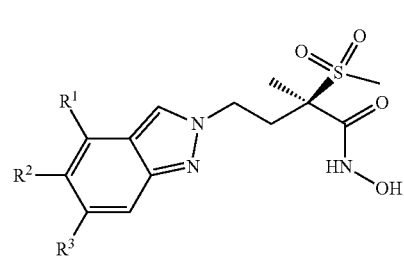

(A1)

wherein $R^1$ is H or halogen; $R^2$ is $(C_3-C_4)$alkynyloxy or the group M; $R^3$ is H or halogen; M is one of the groups $M^A$ and $M^B$ represented below

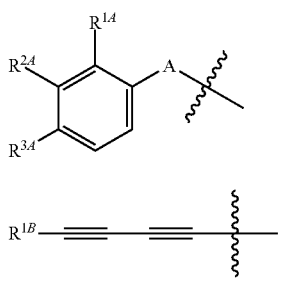

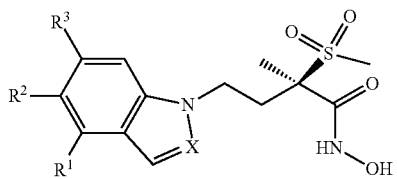

wherein A is a bond, CH$_2$CH$_2$, CH=CH or C≡C; R$^{1A}$ represents H or halogen; R$^{2A}$ represents H, alkoxy or halogen; R$^{3A}$ represents H, alkoxy, hydroxyalkoxy, thioalkoxy, trifluoromethoxy, amino, dialkylamino, hydroxyalkyl, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxyalkyl)oxetan-3-yl, 3-aminooxetan-3-yl, 3-(dialkylamino)oxetan-3-yl, 3-hydroxythietan-3-yl, morpholin-4-ylalkoxy, morpholin-4-ylalkyl, oxazol-2-yl or [1,2,3]triazol-2-yl; and R$^{1B}$ represents 3-hydroxyoxetan-3-yl, 3-hydroxythietan-3-yl, hydroxyalkyl, aminoalkyl, trans-2-hydroxymethyl-cycloprop-1-yl or 4-hydroxytetrahydro-2H-pyran-4-yl.

In WO 2015/091741, we have reported antibacterial 1H-indazole derivatives of general formula (A2)

(A2)

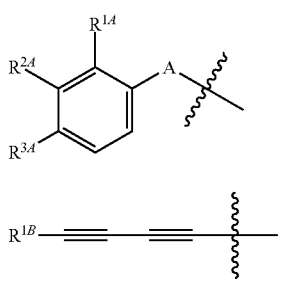

wherein
X represents N or CH;
R$^1$ represents H or halogen;
R$^2$ represents (C$_3$-C$_4$)alkynyloxy or the group M;
R$^3$ represents H or halogen;
M is one of the groups M$^A$ and M$^B$ represented below

M$^A$

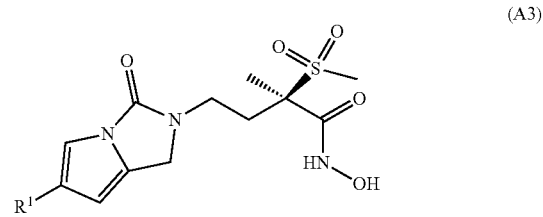

M$^B$ wherein A represents a bond, CH$_2$CH$_2$, CH=CH or C≡C; R$^{1A}$ represents H or halogen; R$^{2A}$ represents H, (C$_1$-C$_3$)alkoxy or halogen; R$^{3A}$ represents H, (C$_1$-C$_3$)alkoxy, hydroxy(C$_1$-C$_4$)alkoxy, (C$_1$-C$_3$)thioalkoxy, trifluoromethoxy, amino, hydroxy(C$_1$-C$_4$)alkyl, 2-hydroxyacetamido, 1-hydroxymethyl-cycloprop-1-yl, trans-2-hydroxymethyl-cycloprop-1-yl, 1,2-dihydroxyethyl, 3-hydroxyoxetan-3-yl, 3-(hydroxy(C$_1$-C$_3$)alkyl)oxetan-3-yl, 3-aminooxetan-3-yl, 3-hydroxythietan-3-yl, morpholin-4-yl(C$_2$-C$_3$)alkoxy, morpholin-4-yl-(C$_1$-C$_2$)alkyl, oxazol-2-yl or [1,2,3]triazol-2-yl; and R$^{1B}$ represents 3-hydroxyoxetan-3-yl, 3-hydroxythietan-3-yl, hydroxy(C$_1$-C$_3$)alkyl, amino(C$_1$-C$_3$)alkyl, 1-hydroxymethyl-cycloprop-1-yl or trans-2-hydroxymethyl-cycloprop-1-yl.

In WO 2015/132228, we have reported antibacterial 1,2-dihydro-3H-pyrrolo[1,2-c]imidazol-3-one derivatives of general formula (A3)

(A3)

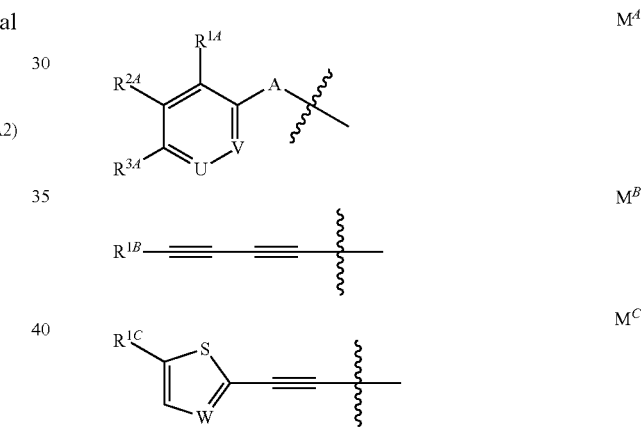

wherein R$^1$ is the group M; M is one of the groups M$^A$, M$^B$ and M$^C$ represented below

M$^A$

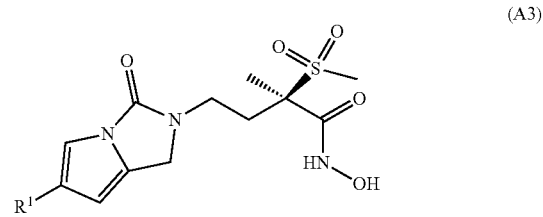

M$^B$

M$^C$ wherein A is a bond, CH=CH or C≡C; U is N or CH; V is N or CH; R$^{1A}$ is H or halogen; R$^{2A}$ is H, (C$_1$-C$_3$)alkoxy or halogen; R$^{3A}$ is H, (C$_1$-C$_3$)alkoxy, hydroxy(C$_2$-C$_4$)alkoxy, dihydroxy(C$_3$-C$_4$)alkoxy, (C$_1$-C$_3$)alkoxy(C$_1$-C$_3$)alkoxy, (C$_1$-C$_3$)thioalkoxy, trifluoromethoxy, trifluoromethyl, amino, hydroxy(C$_1$-C$_4$)alkyl, 1,2-dihydroxyethyl, 1-hydroxy-2,2-difluoroethyl, (C$_1$-C$_3$)alkoxy(C$_1$-C$_4$)alkyl, 2-hydroxy-1-oxoethyl, [(C$_1$-C$_4$)alkoxy]carbonyl, methylsulfonamidomethyl, 3-hydroxy-3-methylbut-1-yn-1-yl, 2-hydroxyacetamido, (carbamoyloxy)methyl, 1-aminocyclopropyl, 1-hydroxymethyl-cycloprop-1-yl, 1-aminomethyl-cycloprop-1-yl, 1-(((dimethylglycyl)oxy)methyl)-cycloprop-1-yl, 1-aminomethyl-cycloprop-1-yl, 1-(carbamoyloxy)methyl-cycloprop-1-yl, 1-(morpholin-4-yl)methylcycloprop-1-yl, trans-2-hydroxymethyl-cycloprop-1-yl, 1-(hydroxymethyl)-cyclobut-1-yl, 1-(2-hydroxyacetyl)azetidin-3-yl, (1-tert-butyloxycarbonyl)-3-hydroxyazetidin-3-yl, 3-hydroxyoxetan-3-yl, 3-(hydroxy(C$_1$-C$_3$)alkyl)oxetan-3-yl, 3-aminooxetan-3-yl, 3-hydroxythietan-3-yl, 4-aminopiperidin-1-yl, morpholin-4-yl(C$_2$-C$_3$)alkoxy, [4-N—(C$_1$-C$_3$)alkylpiperazin-1-yl](C$_1$-C$_3$)alkyl, morpholin-4-yl-(C$_1$-C$_2$)alkyl, [1,2,3]triazol-2-yl, 3-[hydroxy($C_2$-$C_3$)alkyl]-2-oxo-imidazolidin-1-yl, (1s,3r)-(1-hydroxy-3-(hydroxymethyl)cyclobutyl)methyl, (4-hydroxypiperidinyl)methyl or (4-aminopiperidinyl)methyl; and $R^{1B}$ is 3-hydroxyoxetan-3-yl, 3-hydroxythietan-3-yl, 3-(hydroxy($C_1$-$C_3$)alkyl)oxetan-3-yl, hydroxy($C_1$-$C_3$)alkyl, 1,2-dihydroxyethyl, amino($C_1$-$C_3$)alkyl, (dimethylamino)methyl, methylsulfonamidomethyl, 1-aminocyclopropyl, 1-hydroxymethyl-cycloprop-1-yl, 1-(carbamoyloxy)methyl-cycloprop-1-yl, 1-(((dimethylglycyl)oxy)methyl)-cycloprop-1-yl, 1-((phosphonooxy)methyl)-cycloprop-1-yl, 1-((((phosphonooxy)methoxy)carbonyl)oxymethyl)-cycloprop-1-yl, 1-((((phosphonooxy)methoxy)carbonyl)amino)-cycloprop-1-yl, trans-2-hydroxymethyl-cycloprop-1-yl, 1-fluoro-2-hydroxymethyl-cycloprop-1-yl, 2-fluoro-2-hydroxymethyl-cycloprop-1-yl, 1-methyl-2-hydroxymethyl-cycloprop-1-yl, 2-hydroxymethyl-2-methylcycloprop-1-yl, (1R*,2S*,3s*)-1,2-bis-(hydroxymethyl)-cycloprop-3-yl, 1-(hydroxymethyl)cyclobut-1-yl, 3-amino-oxetan-3-yl, 3-(hydroxy($C_1$-$C_3$)alkyl)oxetan-3-yl, 1-(2-hydroxyacetyl)-azetidin-3-yl, trans-(cis-3,4-dihydroxy)-cyclopent-1-yl, 3-hydroxymethylbicyclo[1,1,1]pentan-1-yl, 4-hydroxy-tetrahydro-2H-pyran-4-yl, 5-aminotetrahydro-2H-pyran-2-yl, 3-hydroxyoxetan-3-ylmethyl, 1-cyclobutyl-2-hydroxyethyl or 1-(oxetan-3-yl)-azetidin-3-yl.

In WO 2015/173329, we have reported antibacterial quinazoline-4(3H)-one derivatives of general formula (A4)

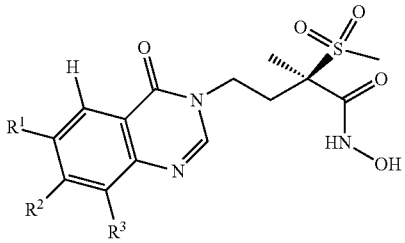

(A4)

wherein $R^1$ is H or halogen; $R^2$ is the group M; $R^3$ is H or halogen; M is one of the groups $M^A$ and $M^B$ represented below

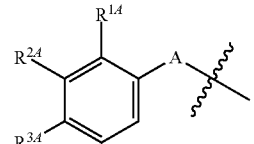

$M^A$

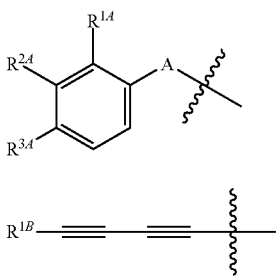

$M^B$ wherein A represents a bond or C≡C; $R^{1A}$ is H or halogen; $R^{2A}$ is H, ($C_1$-$C_3$)alkoxy or halogen; $R^{3A}$ is H, ($C_1$-$C_3$)alkoxy, hydroxy($C_2$-$C_4$)alkoxy, hydroxy($C_1$-$C_4$)alkyl, 1,2-dihydroxyethyl, di($C_1$-$C_3$)alkylamino, 1-hydroxymethyl-cycloprop-1-yl, 1-((dimethylglycyl)oxy)methyl-cycloprop-1-yl, 3-hydroxyoxetan-3-yl, morpholin-4-yl-($C_1$-$C_2$)alkyl or morpholin-4-yl($C_2$-$C_3$)alkoxy; and $R^{1B}$ is hydroxy($C_1$-$C_3$)alkyl, amino($C_1$-$C_3$)alkyl, [di($C_1$-$C_3$)alkylamino]-($C_1$-$C_3$)alkyl, 1,2-dihydroxyprop-3-yl, 1-amino-cycloprop-1-yl, 1-hydroxymethyl-cycloprop-1-yl, 1-((phosphonooxy)methyl)cycloprop-1-yl, trans-2-hydroxymethyl-cycloprop-1-yl, trans-2-aminomethyl-cycloprop-1-yl, 1-fluoro-2-hydroxymethyl-cycloprop-1-yl, trans-2-hydroxymethyl-1-methyl-cycloprop-1-yl, 2-fluoro-2-hydroxymethyl-cycloprop-1-yl, trans-2-hydroxymethyl-2-methyl-cycloprop-1-yl, 1-(1,2-dihydroxyethyl)-cycloprop-1-yl, trans-2-(1,2-dihydroxyethyl)-cycloprop-1-yl, 1-(hydroxymethyl)cyclobut-1-yl, 3-hydroxyoxetan-3-yl, 3-(hydroxy($C_1$-$C_3$)alkyl)oxetan-3-yl, 3-hydroxythietan-3-yl, trans-(cis-3,4-dihydroxy)-cyclopent-1-yl, 3-(2-aminoacetamido)cyclopentyl or 3-hydroxymethylbicyclo[1,1,1]pentan-1-yl.

In WO 2016/079688, we have reported antibacterial benzothiazole derivatives of general formula (A5)

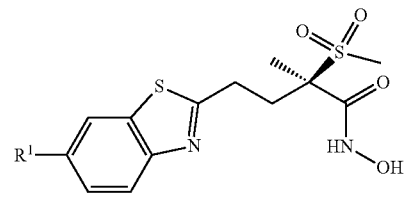

(A5)

wherein
$R^1$ is the group M, whereby M is one of the groups $M^A$ and $M^B$ represented below

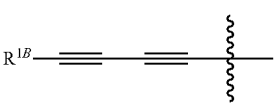

$M^A$

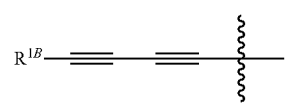

$M^B$ wherein A represents a bond or C≡C;
$R^{1A}$ is H or halogen;
$R^{2A}$ is H or halogen; and
$R^{3A}$ is H, ($C_1$-$C_3$)alkoxy, hydroxy($C_2$-$C_4$)alkoxy, hydroxy($C_1$-$C_4$)alkyl, dihydroxy($C_2$-$C_4$)alkyl, 2-hydroxyacetamido, 1-hydroxymethyl-cycloprop-1-yl, trans-2-hydroxymethyl-cycloprop-1-yl, 3-hydroxyoxetan-3-yl, 3-(hydroxy($C_1$-$C_3$)alkyl)oxetan-3-yl, 3-aminooxetan-3-yl or 1-aminocycloprop-1-yl; and wherein $R^{1B}$ is hydroxy($C_1$-$C_4$)alkyl, dihydroxy($C_2$-$C_4$)alkyl, amino($C_1$-$C_4$)alkyl, di($C_1$-$C_4$)alkylamino($C_1$-$C_3$)alkyl, 1-amino-cycloprop-1-yl, 1-hydroxymethyl-cycloprop-1-yl, trans-2-hydroxymethyl-cycloprop-1-yl, trans-2-aminomethyl-cycloprop-1-yl, trans-2-hydroxymethyl-1-methyl-cycloprop-1l-yl, trans-2-hydroxymethyl-2-methyl-cycloprop-1-yl, cis-1-fluoro-2-(hydroxymethyl)cycloprop-1-yl, cis-2-fluoro-2-(hydroxymethyl)cycloprop-1l-yl, 2-(1,2-dihydroxyethyl)-cycloprop-1-yl, 1-(hydroxymethyl)-cyclobutan-1-yl, cis-3-(hydroxymethyl)-1-hydroxy-cyclobutan-1-yl, 3-hydroxyoxetan-3-yl, 3-hydroxyoxetan-3-yl-($C_1$-$C_3$)alkyl, 3-aminooxetan-3-yl, 3-hydroxymethyl-oxetan-3-yl, trans-(cis-3,4-dihydroxy)-cyclopent-1-yl, 3-hydroxymethylbicyclo[1,1,1]pentan-1-yl, 4-hydroxytetrahydro-2H-pyran-4-yl, (3R,6S)-3-aminotetrahydro-2H-pyran-6-yl, piperidin-4-yl, 1-(2-hydroxyacetyl)piperidin-4-yl, 3-hydroxythietan-3-yl, 1-(2-hydroxyacetyl)azetidin-3-yl or 1-glycylazetidin-3-yl; and salts thereof.

Besides, in Montgomery et al., *J. Med. Chem.* (2012), 55(4), 1662-1670, yet further LpxC inhibitors are disclosed, among others the compound of formula (A6)

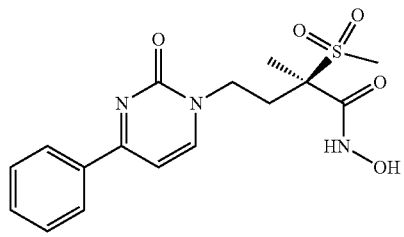
(A6)

The instant invention provides new antibacterial 1,2-dihydro-3H-pyrrolo[1,2-c]imidazol-3-one derivatives, namely the compounds of formula I described herein.

Various embodiments of the invention are presented hereafter:

1) The invention relates to compounds of formula I

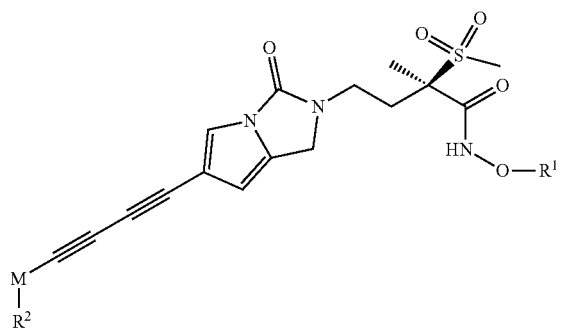
I wherein

M is one of the groups $M^A$, $M^B$ and $M^C$ represented below

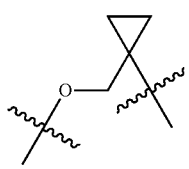
$M^A$

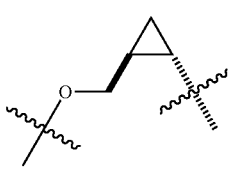
$M^B$

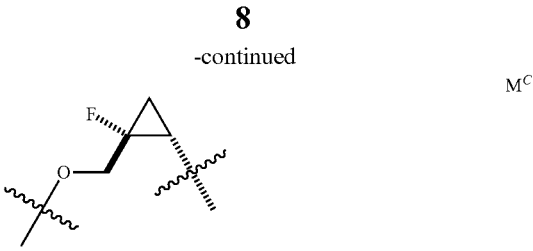
$M^C$ and either $R^1$ represents H and, when M is $M^A$, $R^2$ represents $SO_3H$, phosphonooxymethyl or the group $L^{2A}$ represented below

$L^{2A}$ wherein $R^{2A}$ represents $(C_1-C_4)$alkylamino$(C_1-C_4)$alkyl, [di$(C_2-C_4)$alkylamino]methyl, {(methyl)[$(C_2-C_4)$alkyl]amino}methyl, [di$(C_1-C_4)$alkylamino]$(C_2-C_4)$alkyl, morpholin-4-yl-$(C_1-C_4)$alkyl, phosphonooxy$(C_1-C_4)$alkyl, phosphonooxymethoxy, 2-(phosphonooxy-$(C_1-C_4)$alkyl)-phenyl, (2-(phosphonooxy)-phenyl)-$(C_1-C_4)$alkyl (especially 2-(2-(phosphonooxy)phenyl)ethyl) or [2-(phosphonooxy-$(C_1-C_4)$alkyl)-phenyl]-$(C_1-C_4)$alkyl, or, when M is $M^B$ or $M^C$, $R^2$ represents $PO_3H_2$, $SO_3H$, phosphonooxymethyl or the group $L^{2BC}$ represented below

$L^{2BC}$ wherein $R^{2BC}$ represents $(C_1-C_4)$alkylamino$(C_1-C_4)$alkyl, [di$(C_1-C_4)$alkylamino]$(C_1-C_4)$alkyl, morpholin-4-yl-$(C_1-C_4)$alkyl, phosphonooxy$(C_1-C_4)$alkyl, phosphonooxymethoxy, 2-(phosphonooxy-$(C_1-C_4)$alkyl)-phenyl, (2-(phosphonooxy)-phenyl)-$(C_1-C_4)$alkyl (especially 2-(2-(phosphonooxy)phenyl)ethyl) or [2-(phosphonooxy-$(C_1-C_4)$alkyl)-phenyl]-$(C_1-C_4)$alkyl, or $R^2$ represents H and $R^1$ represents $PO_3H_2$, $SO_3H$, phosphonooxymethyl or the group $L^1$ represented below $L^1$ wherein $R^{1A}$ represents $(C_1-C_4)$alkylamino$(C_1-C_4)$alkyl, [di$(C_1-C_4)$alkylamino]$(C_1-C_4)$alkyl, morpholin-4-yl-$(C_1-C_4)$alkyl, phosphonooxy$(C_1-C_4)$alkyl, phosphonooxymethoxy, 2-(phosphonooxy-$(C_1-C_4)$alkyl)-phenyl, (2-(phosphonooxy)-phenyl)-$(C_1-C_4)$alkyl (especially 2-(2-(phosphonooxy)phenyl)ethyl) or [2-(phosphonooxy-$(C_1-C_4)$alkyl)-phenyl]-$(C_1-C_4)$alkyl;

it being understood that the molecule is always such that its $R^2$ group is attached to the oxygen atom of its $M^A$, $M^B$ and $M^C$ group;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "$(C_x\text{-}C_y)$ alkyl" (x and y each being an integer) refers to a straight or branched chain alkyl group containing x to y carbon atoms. For example, a $(C_1\text{-}C_3)$alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkylamino", used alone or in combination, refers to an amino group wherein one of the two hydrogen atoms has been replaced by an alkyl group as defined before. The term "$(C_x\text{-}C_y)$alkylamino" (x and y each being an integer) refers to an alkylamino group as defined before wherein the alkyl group contains x to y carbon atoms. For example, a $(C_1\text{-}C_4)$alkylamino group is an alkylamino group as defined before wherein the alkyl group contains from one to four carbon atoms. Representative examples of alkylamino groups include methylamino, ethylamino and iso-propylamino. Preferred are methylamino and ethylamino. Most preferred is methylamino.

The term "dialkylamino", used alone or in combination, refers to an amino group wherein each hydrogen atom has been replaced by an alkyl group as defined before, whereby the alkyl groups may be the same or different. The term "di$(C_x\text{-}C_y)$alkylamino" (x and y each being an integer) refers to a dialkylamino group as defined before wherein each alkyl group independently contains x to y carbon atoms. For example, a di$(C_1\text{-}C_4)$ alkylamino group is a dialkylamino group as defined before wherein each alkyl group independently contains from one to four carbon atoms. Representative examples of dialkylamino groups include dimethylamino, diethylamino, N-ethyl-N-methyl-amino and N-iso-propyl-N-methyl-amino. Preferred are dimethylamino and diethylamino. Most preferred is dimethylamino.

The term "$(C_1\text{-}C_4)$alkylamino-$(C_1\text{-}C_4)$alkyl" refers to an alkyl group containing from one to four carbon atoms as defined before wherein one of the hydrogen atoms has been replaced by a $(C_1\text{-}C_4)$alkylamino group as defined before. Representative examples of $(C_1\text{-}C_4)$ alkylamino-$(C_1\text{-}C_4)$alkyl groups include methylaminomethyl, 2-methylamino-ethyl, 2-methylaminoeth-2-yl, 3-methylamino-prop-2-yl, 3-methylamino-prop-3-yl, 4-methylamino-but-2-yl, 4-methylamino-but-3-yl, 4-methylamino-but-4-yl, ethylaminomethyl, 2-ethylamino-ethyl, 2-ethylamino-eth-2-yl, 2-ethylamino-prop-2-yl, 3-ethylamino-prop-2-yl, 2-ethylamino-prop-3-yl, 3-ethylamino-prop-3-yl, 4-ethylamino-but-3-yl, 4-ethylamino-but-4-yl, n-propylaminomethyl and 2-(n-propylamino)-ethyl; preferred are methylaminomethyl, 2-methylamino-eth-2-yl and 3-methylamino-prop-3-yl; most preferred is methylaminomethyl.

The term "[di$(C_x\text{-}C_y)$alkylamino]-methyl" (x and y each being an integer) refers to a methyl group wherein one of the hydrogen atoms has been replaced by a di$(C_x\text{-}C_y)$alkylamino group as defined before. Representative examples of [di$(C_2\text{-}C_4)$alkylamino]-methyl groups thus include diethylaminomethyl, di(n-propyl)aminomethyl, di(iso-propyl)aminomethyl and 3-(di(n-butyl)amino)-methyl; preferred are diethylaminomethyl and di(n-propyl)aminomethyl; most preferred is diethylaminomethyl.

The term "{(methyl)[$(C_2\text{-}C_4)$alkyl]amino}methyl" (x and y each being an integer) refers to a methyl group wherein one of the hydrogen atoms has been replaced by a nitrogen atom, which nitrogen atom bears both a methyl group and a $(C_2\text{-}C_4)$alkyl group as defined before. Representative examples of {(methyl)[$(C_2\text{-}C_4)$ alkyl]amino}methyl groups thus include ethyl(methyl)amino-methyl, (n-propyl)(methyl)amino-methyl, (iso-propyl)(methyl)amino-methyl and (n-butyl)(methyl)amino-methyl; preferred is ethyl(methyl)amino-methyl.

The term "[di$(C_x\text{-}C_y)$alkylamino]-$(C_m\text{-}C_n)$alkyl" (x, y, m and n each being an integer) refers to an alkyl group containing from m to n carbon atoms as defined before wherein one of the hydrogen atoms has been replaced by a di$(C_x\text{-}C_y)$alkylamino group as defined before. Representative examples of [di$(C_1\text{-}C_4)$alkylamino]-$(C_1\text{-}C_4)$alkyl groups thus include dimethylaminomethyl, 2-(dimethylamino)-ethyl, 2-(dimethylamino)-eth-2-yl, 3-(dimethylamino)-propyl, 3-(dimethylamino)-prop-2-yl, 3-(dimethylamino)-prop-3-yl, 4-(dimethylamino)-butyl, 4-(dimethylamino)-but-2-yl, 4-(dimethylamino)-but-3-yl, 4-(dimethylamino)-but-4-yl, diethylaminomethyl, 2-(diethylamino)-ethyl, 2-(diethylamino)-eth-2-yl, 3-(diethylamino)-propyl, 3-(diethylamino)-prop-3-yl, 4-(diethylamino)-butyl, di(n-propyl)aminomethyl, 2-(di(n-propyl)amino)-ethyl and 3-(di(n-propyl)amino)-propyl; preferred are dimethylaminomethyl, 2-(dimethylamino)-ethyl and 3-(dimethylamino)-propyl; most preferred is dimethylaminomethyl. Representative examples of [di$(C_1\text{-}C_4)$alkylamino]-$(C_2\text{-}C_4)$alkyl groups include 2-(dimethylamino)-ethyl, 2-(dimethylamino)-eth-2-yl, 3-(dimethylamino)-propyl, 3-(dimethylamino)-prop-2-yl, 3-(dimethylamino)-prop-3-yl, 4-(dimethylamino)-butyl, 4-(dimethylamino)-but-2-yl, 4-(dimethylamino)-but-3-yl, 4-(dimethylamino)-but-4-yl, diethylaminomethyl, 2-(diethylamino)-ethyl, 2-(diethylamino)-eth-2-yl, 3-(diethylamino)-propyl, 3-(diethylamino)-prop-3-yl, 4-(diethylamino)-butyl, di(n-propyl)aminomethyl, 2-(di(n-propyl)amino)-ethyl and 3-(di(n-propyl)amino)-propyl; preferred are 2-(dimethylamino)-ethyl and 3-(dimethylamino)-propyl; most preferred is 2-(dimethylamino)-ethyl.

The term "morpholin-4-yl-$(C_1\text{-}C_4)$alkyl" refers to a $(C_1\text{-}C_4)$alkyl group as defined before wherein one of the hydrogen atoms has been replaced by a morpholin-4-yl group. Examples of morpholin-4-yl-$(C_1\text{-}C_4)$alkyl groups are morpholin-4-ylmethyl and 2-morpholin-4-yl-ethyl. The most preferred morpholin-4-yl$(C_1\text{-}C_4)$ alkyl group is morpholin-4-ylmethyl.

The term "quinolone-resistant", when used in this text, refers to a bacterial strain against which ciprofloxacin has a Minimal Inhibitory Concentration of at least 16 mg/L (said Minimal Inhibitory Concentration being measured with the standard method described in "*Methods for Dilution Antimicrobial Susceptibility Tests for Bacteria that Grow Aerobically*", Approved standard, 7th ed., Clinical and Laboratory Standards Institute (CLSI) Document M7-A7, Wayne, Pa., USA (2006)).

The term "carbapenem-resistant", when used in this text, refers to a bacterial strain against which imipenem has a Minimal Inhibitory Concentration of at least 16 mg/L (said Minimal Inhibitory Concentration being measured with the standard method described in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA (2006)).

The term "multi-drug resistant", when used in this text, refers to a bacterial strain against which at least three antibiotic compounds selected from three distinct antibiotic categories have Minimal Inhibitory Concentrations (MICs) over their respective clinical breakpoints, whereby said three distinct antibiotic categories are chosen among penicillins, combinations of penicillins with beta-lactamase inhibitors, cephalosporins, carbapenems, monobactams, fluoro-quinolones, aminoglycosides, phosphonic acids, tetracyclins and polymixins. Clinical breakpoints are defined according to the latest available list published by Clinical and Laboratory Standards Institute (Wayne, Pa., USA). Accordingly, clinical breakpoints are the levels of MIC at which, at a given time, a bacterium is deemed either susceptible or resistant to treatment by the corresponding antibiotic or antibiotic combination.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH (2008) and 'Pharmaceutical Salts and Co-crystals', Johan Wouters and Luc Qudrd (Eds.), RSC Publishing (2012).

In this text, a bond interrupted by a wavy line shows a point of attachment of the radical drawn to the rest of the molecule. For example, the radical drawn below

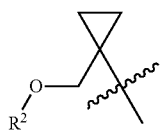

wherein $R^2$ is $PO_3H_2$ the phosphonooxymethylcycloprop-1-yl radical.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention in particular relates to compounds of formula I according to embodiment 1) which are also compounds of formula $I_{CE}$

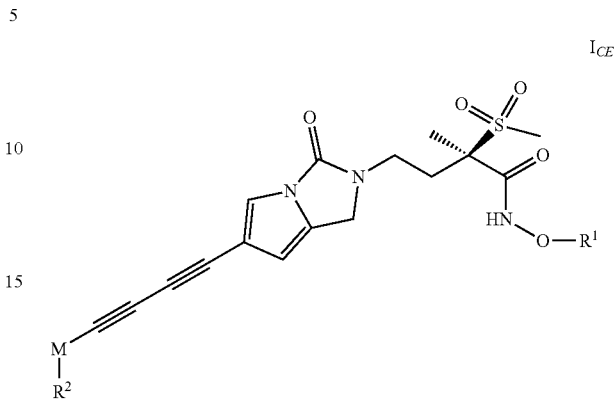

$I_{CE}$ wherein

M is one of the groups $M^A$, $M^B$ and $M^C$ represented below

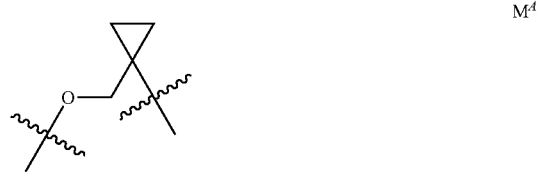

$M^A$

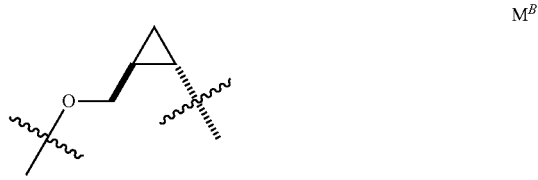

$M^B$

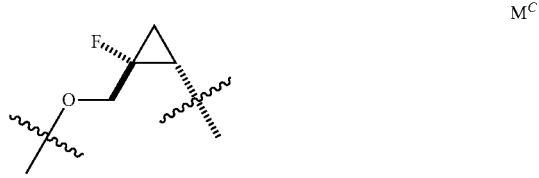

$M^C$ and either $R^1$ represents H and, when M is $M^A$, $R^2$ represents $SO_3H$ or the group $L^{2A}$ represented below

$L^{2A}$ wherein, $R^{2A}$ represents morpholin-4-yl-$(C_1$-$C_4)$alkyl or (2-(phosphonooxy)-phenyl)-$(C_1$-$C_4)$alkyl (especially 2-(2-(phosphonooxy)phenyl)ethyl), or, when M is $M^B$ or $M^C$, $R^2$ represents $PO_3H_2$ or the group $L^{2BC}$ represented below

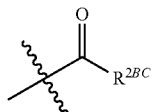
$L^{2BC}$ wherein, $R^{2BC}$ represents (2-(phosphonooxy)-phenyl)-($C_1$-$C_4$)alkyl (especially 2-(2-(phosphonooxy)phenyl)ethyl), or $R^2$ represents H and $R^1$ represents $PO_3H_2$ or the group $L^1$ represented below

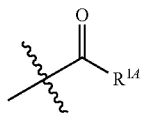
$L^1$ wherein $R^{1A}$ represents (2-(phosphonooxy)-phenyl)-($C_1$-$C_4$) alkyl (especially 2-(2-(phosphonooxy)phenyl)ethyl);
it being understood that the molecule is always such that its $R^2$ group is attached to the oxygen atom of its $M^A$, $M^B$ and $M^C$ group;
and to salts (in particular pharmaceutically acceptable salts) of compounds of formula $I_{CE}$.

3) In particular, the compounds of formula $I_{CE}$ according to embodiment 2) will be such that either $R^1$ represents H and, when M is $M^A$, $R^2$ represents $SO_3H$ or the group $L^{2A}$ represented below

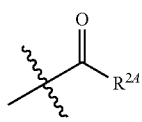
$L^{2A}$ wherein, $R^{2A}$ represents morpholin-4-ylmethyl or 2-(2-(phosphonooxy)phenyl)ethyl, or, when M is $M^B$ or $M^C$, $R^2$ represents $PO_3H_2$ or the group $L^{2BC}$ represented below

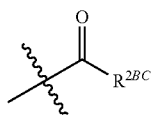
$L^{2BC}$ wherein, $R^{2BC}$ represents 2-(2-(phosphonooxy)phenyl)ethyl, or $R^2$ represents H and $R^1$ represents $PO_3H_2$ or the group $L^1$ represented below

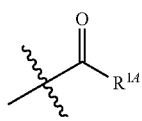
$L^1$ wherein $R^{1A}$ represents 2-(2-(phosphonooxy)phenyl)ethyl.
4) According to one main embodiment of this invention, the compounds of formula I as defined in embodiment 1) or 2) will be such that M is the group $M^A$.

5) One sub-embodiment of embodiment 4) relates to the compounds of formula I as defined in embodiment 4) wherein $R^1$ represents H.
6) Preferably, the compounds of formula I according to embodiment 5) will be such that $R^1$ represents H and $R^2$ represents $SO_3H$ or the group $L^{2A}$ wherein $R^{2A}$ represents morpholin-4-yl-($C_1$-$C_4$)alkyl or (2-(phosphonooxy)-phenyl)-($C_1$-$C_4$)alkyl (especially 2-(2-(phosphonooxy)phenyl) ethyl).
7) More preferably, the compounds of formula I according to embodiment 5) will be such that $R^1$ represents H and $R^2$ represents $SO_3H$ or the group $L^{2A}$ wherein $R^{2A}$ represents morpholin-4-ylmethyl or 2-(2-(phosphonooxy)phenyl)ethyl.
8) Another sub-embodiment of embodiment 4) relates to the compounds of formula I as defined in embodiment 4) wherein $R^2$ represents H.
9) Preferably, the compounds of formula I according to embodiment 8) will be such that $R^2$ represents H and $R^1$ represents $PO_3H_2$ or the group $L^1$ wherein $R^{1A}$ represents 2-(2-(phosphonooxy)phenyl)ethyl.
10) According to another main embodiment of this invention, the compounds of formula I as defined in embodiment 1) or 2) will be such that M is the group $M^B$.
11) One sub-embodiment of embodiment 10) relates to the compounds of formula I as defined in embodiment 10) wherein $R^1$ represents H.
12) Preferably, the compounds of formula I according to embodiment 11) will be such that $R^1$ represents H and $R^2$ represents $PO_3H_2$ or the group $L^{2BC}$ wherein $R^{2BC}$ represents 2-(2-(phosphonooxy)phenyl)ethyl.
13) Another sub-embodiment of embodiment 10) relates to the compounds of formula I as defined in embodiment 10) wherein $R^2$ represents H.
14) According to yet another main embodiment of this invention, the compounds of formula I as defined in embodiment 1) or 2) will be such that M is the group $M^C$.
15) One sub-embodiment of embodiment 14) relates to the compounds of formula I as defined in embodiment 14) wherein $R^1$ represents H.
16) Preferably, the compounds of formula I according to embodiment 15) will be such that $R^1$ represents H and $R^2$ represents $PO_3H_2$.
17) Another sub-embodiment of embodiment 14) relates to the compounds of formula I as defined in embodiment 14) wherein $R^2$ represents H.
18) In a preferred embodiment, the compounds of formula I according to embodiment 1) will be such that:
M is the group $M^A$, $R^1$ represents H and $R^2$ represents $SO_3H$ or the group $L^{2A}$ wherein $R^{2A}$ represents morpholin-4-yl-($C_1$-$C_4$)alkyl or (2-(phosphonooxy)-phenyl)-($C_1$-$C_4$)alkyl (especially 2-(2-(phosphonooxy) phenyl)ethyl); or
M is the group $M^A$, $R^2$ represents H and $R^1$ represents $PO_3H_2$ or the group $L^1$ wherein $R^{1A}$ represents (2-(phosphonooxy)-phenyl)-($C_1$-$C_4$)alkyl (especially 2-(2-(phosphonooxy)phenyl)ethyl); or
M is the group $M^B$, $R^1$ represents H and $R^2$ represents $PO_3H_2$ or the group $L^{2BC}$ wherein $R^{2BC}$ represents (2-(phosphonooxy)-phenyl)-($C_1$-$C_4$)alkyl (especially 2-(2-(phosphonooxy)phenyl)ethyl); or
M is the group $M^C$, $R^1$ represents H and $R^2$ represents $PO_3H_2$.
19) In a more preferred embodiment, the compounds of formula I according to embodiment 1) will be such that:

M is the group $M^A$, $R^1$ represents H and $R^2$ represents $SO_3H$ or the group $L^{2A}$ wherein $R^{2A}$ represents morpholin-4-ylmethyl or 2-(2-(phosphonooxy)phenyl)ethyl; or M is the group $M^A$, $R^2$ represents H and $R^1$ represents $PO_3H_2$ or the group $L^1$ wherein $R^{1A}$ represents 2-(2-(phosphonooxy)phenyl)ethyl; or M is the group $M^B$, $R^1$ represents H and $R^2$ represents $PO_3H_2$ or the group $L^{2BC}$ wherein $R^{1A}$ represents 2-(2-(phosphonooxy)phenyl)ethyl; or M is the group $M^C$, $R^1$ represents H and $R^2$ represents $PO_3H_2$.

20) Another embodiment of this invention relates to compounds of formula I as defined in one of embodiments 1) to 19) as well as to isotopically labelled, especially $^2H$ (deuterium) labelled compounds of formula I as defined in one of embodiments 1) to 19), which compounds are identical to the compounds of formula I as defined in one of embodiments 1) to 19) except that one or more atoms has or have each been replaced by an atom having the same atomic number but an atomic mass different from the atomic mass usually found in nature. Isotopically labelled, especially $^2H$ (deuterium) labelled compounds of formula I and salts (in particular pharmaceutically acceptable salts) thereof are thus within the scope of the present invention. Substitution of hydrogen with the heavier isotope $^2H$ (deuterium) may lead to greater metabolic stability, resulting e.g. in an increased in-vivo half-life, reduced dosage requirements, or an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

21) Particularly preferred are the following compounds of formula I as defined in embodiment 1) or 2):

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 2-morpholinoacetate;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate;

(R)-2-(3-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate;

((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;

((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate;

((1R,2R)-1-fluoro-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;

(R)-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy)phosphonic acid;

(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl hydrogen sulfate;

as well as the salts (in particular the pharmaceutically acceptable salts) thereof.

22) The invention further relates to the groups of compounds of formula I selected from the group consisting of the compounds listed in embodiment 21), which groups of compounds furthermore correspond to one of embodiments 4) to 19), as well as to the salts (in particular the pharmaceutically acceptable salts) of such compounds. The invention moreover relates to any individual compound of formula I selected from the group consisting of the compounds listed in embodiment 21), and to the salts (in particular the pharmaceutically acceptable salts) of such individual compound.

The compounds of formula I according to this invention, i.e. according to one of embodiments 1) to 22) above, exhibit antibacterial activity in biological environment (i.e. in the presence of a phosphatase, an esterase, a sulfatase or any suitable equivalent thereof capable of removing the group $R^1$ or $R^2$ that is not hydrogen), especially against Gram-negative organisms and are therefore suitable to treat bacterial infections in mammals, especially humans. Said compounds may also be used for veterinary applications, such as treating infections in livestock and companion animals. They may further constitute substances for preserving inorganic and organic materials in particular all types of organic materials for example polymers, lubricants, paints, fibres, leather, paper and wood.

They may therefore be used for the treatment or prevention of infectious disorders caused by fermentative or non-fermentative gram negative bacteria, especially those caused by susceptible and multi-drug resistant Gram-negative bacteria. Examples of such Gram-negative bacteria include *Acinetobacter* spp. such as *Acinetobacter baumannii* or *Acinetobacter haemolyticus*, *Actinobacillus actinomycetemcomitans*, *Achromobacter* spp. such as *Achromobacter xylosoxidans* or *Achromobacter faecalis*, *Aeromonas* spp. such as *Aeromonas hydrophila*, *Bacteroides* spp. such as *Bacteroides fragilis*, *Bacteroides theataioatamicron*, *Bacteroides distasonis*, *Bacteroides ovatus* or *Bacteroides vulgatus*, *Bartonella hensenae*, *Bordetella* spp. such as *Bordetella pertussis*, *Borrelia* spp. such as *Borrelia Burgdorferi*, *Brucella* spp. such as *Brucella melitensis*, *Burkholderia* spp. such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), carbapenemases (KPCs), cefotaximase-Munich (CTX-M), metallo-beta-lactamases, and AmpC-type beta-lactamases that confer resistance to currently available cephalosporins, cephamycins, carbapenems, beta-lactams, and beta-lactam/beta-lactamase inhibitor combinations), *Klebsiella rhinoscleromatis* or *Klebsiella* ozaenae, *Legionella pneumophila, Mannheimia haemolyticus, Moraxella catarrhalis* (beta-lactamase positive and negative), *Morganella morganii, Neisseria* spp. such as *Neisseria gonorrhoeae* or *Neisseria meningitidis, Pasteurella* spp. such as *Pasteurella multocida, Plesiomonas shigelloides, Porphyromonas* spp. such as *Porphyromonas asaccharolytica, Prevotella* spp. such as *Prevotella corporis, Prevotella intermedia* or *Prevotella endodontalis, Proteus* spp. such as *Proteus mirabilis, Proteus vulgaris, Proteus penneri* or *Proteus myxofaciens, Porphyromonas asaccharolytica, Plesiomonas shigelloides, Providencia* spp. such as *Providencia stuartii, Providencia rettgeri* or *Providencia alcalifaciens, Pseudomonas* spp. such as *Pseudomonas aeruginosa* (including ceftazidime-, cefpirome- and cefepime-resistant *P. aeruginosa*, carbapenem-resistant *P. aeruginosa* or quinolone-resistant *P. aeruginosa*) or *Pseudomonas fluorescens, Ricketsia prowazekii, Salmonella* spp. such as *Salmonella typhi* or *Salmonella paratyphi, Serratia marcescens, Shigella* spp. such as *Shigella flexneri, Shigella boydii, Shigella sonnei* or *Shigella dysenteriae, Streptobacillus moniliformis, Stenotrophomonas maltophilia, Treponema* spp., *Vibrio* spp. such as *Vibrio cholerae, Vibrio parahaemolyticus, Vibrio vulnificus, Vibrio alginolyticus, Yersinia* spp. such as *Yersinia enterocolitica, Yersinia pestis* or *Yersinia pseudotuberculosis.*

The compounds of formula I according to this invention are thus useful for treating a variety of infections caused by fermentative or non-fermentative Gram-negative bacteria, especially infections such as: nosocomial pneumonia (related to infection by *Legionella pneumophila, Haemophilus influenzae*, or *Chlamydia pneumoniae*); urinary tract infections; systemic infections (bacteraemia and sepsis); skin and soft tissue infections (including burn patients); surgical infections; intraabdominal infections; lung infections (including those in patients with cystic fibrosis); *Helicobacter pylori* (and relief of associated gastric complications such as peptic ulcer disease, gastric carcinogenesis, etc.); endocarditis; diabetic foot infections; osteomyelitis; otitis media, sinusitus, bronchitis, tonsillitis, and mastoiditis related to infection by *Haemophilus influenzae* or *Moraxella catarrhalis*; pharyngitis, rheumatic fever, and glomerulonephritis related to infection by *Actinobacillus haemolyticum*; sexually transmitted diseases related to infection by *Chlamydia trachormatis, Haemophilus ducreyi, Treponema pallidum, Ureaplasma urealyticum*, or *Neisseria gonorrheae*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae* or *H. influenzae*; gastroenteritis related to infection by *Campylobacter jejuni*; persistent cough related to infection by *Bordetella pertussis* and gas gangrene related to infection by *Bacteroides* spp. Other bacterial infections and disorders related to such infections that may be treated or prevented in accord with the method of the present invention are referred to in J. P. Sanford et al., "*The Sanford Guide to Antimicrobial Therapy*", 26th Edition, (Antimicrobial Therapy, Inc., 1996).

The preceding lists of infections and pathogens are to be interpreted merely as examples and in no way as limiting.

The compounds of formula I according to this invention, or the pharmaceutically acceptable salts thereof, may therefore be used for the preparation of a medicament, and are suitable, for the prevention or treatment of a bacterial infection, in particular for the prevention or treatment of a bacterial infection caused by Gram-negative bacteria, especially by multi-drug resistant Gram-negative bacteria.

The compounds of formula I according to this invention, or the pharmaceutically acceptable salts thereof, may thus especially be used for the preparation of a medicament, and are suitable, for the prevention or treatment of a bacterial infection caused by Gram-negative bacteria selected from the group consisting of *Burkholderia* spp. (e.g. *Burkholderia cepacia*), *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection mediated by quinolone-resistant, carbapenem-resistant or multi-drug resistant *Klebsiella pneumoniae* bacteria).

The compounds of formula I according to this invention, or the pharmaceutically acceptable salts thereof, may more especially be used for the preparation of a medicament, and are suitable, for the prevention or treatment of a bacterial infection caused by Gram-negative bacteria selected from the group consisting of *Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia* and *Pseudomonas aeruginosa* bacteria (notably of a bacterial infection caused by Gram-negative bacteria selected from the group consisting of *Klebsiella pneumoniae* and *Pseudomonas aeruginosa* bacteria, and in particular of a bacterial infection caused by *Pseudomonas aeruginosa* bacteria).

The compounds of formula I according to this invention, or the pharmaceutically acceptable salts thereof, may thus especially be used for the preparation of a medicament, and are suitable, for the prevention or treatment of a bacterial infection selected from urinary tract infections, systemic infections (such as bacteraemia and sepsis), skin and soft tissue infections (including burn patients), surgical infections; intraabdominal infections and lung infections (including those in patients with cystic fibrosis).

The compounds of formula I according to this invention, or the pharmaceutically acceptable salts thereof, may more especially be used for the preparation of a medicament, and are suitable, for the prevention or treatment of a bacterial infection selected from urinary tract infections, intraabdominal infections and lung infections (including those in patients with cystic fibrosis), and in particular for the prevention or treatment of a bacterial infection selected from urinary tract infections and intraabdominal infections.

Besides, the compounds of formula I according to this invention, in a biologically relevant environment (i.e. in the presence of a phosphatase, an esterase, a sulfatase or any suitable equivalent thereof capable of removing the group $R^1$ or $R^2$ that is not hydrogen), display antibacterial properties and have the ability to improve permeability of the outer membrane of Gram-negative bacteria to other antibacterial agents. Their use in combination with another antibacterial agent might offer some further advantages such as lowered side-effects of drugs due to lower doses used or shorter time of treatment, more rapid cure of infection shortening hospital stays, increasing spectrum of pathogens controlled, and decreasing incidence of development of resistance to antibiotics. The antibacterial agent for use in combination with a compound of formula I according to this invention will be selected from the group consisting of a penicillin antibiotic (such as ampicillin, piperacillin, penicillin G, amoxicillin, or ticarcillin), a cephalosporin antibiotic (such as ceftriaxone, cefatazidime, cefepime, cefotaxime) a carbapenem antibiotic (such as imipenem, or meropenem), a monobactam antibiotic (such as aztreonam or carumonam), a fluoroquinolone antibiotic (such as ciprofloxacin, moxifloxacin or levofloxacin), a macrolide antibiotic (such as erythromycin or azithromycin), an aminoglycoside antibiotic (such as amikacin, gentamycin or tobramycin), a glycopeptide antibiotic (such as vancomycin or teicoplanin), a tetracycline antibiotic (such as tetracycline, oxytetracycline, doxycycline, minocycline or tigecycline), and linezolid, clindamycin, telavancin, daptomycin, novobiocin, rifampicin and polymyxin. Preferably, the antibacterial agent for use in combination with a compound of formula I according to this invention will be selected from the group consisting of vancomycin, tigecycline and rifampicin.

The compounds of formula I according to this invention, or the pharmaceutically acceptable salt thereof, may moreover be used for the preparation of a medicament, and are suitable, for the prevention or treatment (and especially the treatment) of infections caused by biothreat Gram negative bacterial pathogens as listed by the US Center for Disease Control (the list of such biothreat bacterial pathogens can be found at the web page http://www.selectagents.gov/SelectAgentsandToxinsList.html), and in particular by Gram negative pathogens selected from the group consisting of *Yersinia pestis, Francisella tularensis* (tularemia), *Burkholderia pseudomallei* and *Burkholderia mallei*.

One aspect of this invention therefore relates to the use of a compound of formula I according to one of embodiments 1) to 22), or of a pharmaceutically acceptable salt thereof, for the manufacture of a medicament for the prevention or treatment of a bacterial infection (in particular one of the previously mentioned infections caused by Gram-negative bacteria, especially by multi-drug resistant Gram-negative bacteria). Another aspect of this invention relates to a compound of formula I according to one of embodiments 1) to 22), or a pharmaceutically acceptable salt thereof, for the prevention or treatment of a bacterial infection (in particular for the prevention or treatment of one of the previously mentioned infections caused by Gram-negative bacteria, especially by multi-drug resistant Gram-negative bacteria). Yet another aspect of this invention relates to a compound of formula I according to one of embodiments 1) to 22), or a pharmaceutically acceptable salt thereof, as a medicament. Yet a further aspect of this invention relates to a pharmaceutical composition containing, as active principle, a compound of formula I according to one of embodiments 1) to 22), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I or $I_{CE}$.

Any reference to a compound of formula I or $I_{CE}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a Gram-negative bacterial infection in a patient, comprising the administration to said patient of a pharmaceutically active amount of a compound of formula I according to one of embodiments 1) to 22) or a pharmaceutically acceptable salt thereof. Accordingly, the invention provides a method for the prevention or the treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by quinolone-resistant, carbapenem-resistant or multi-drug resistant *Klebsiella pneumoniae* bacteria) in a patient, comprising the administration to said patient of a pharmaceutically active amount of a compound of formula I according to one of embodiments 1) to 22) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 22), and to pharmaceutically acceptable salts thereof. It relates furthermore to the use of such compounds as medicaments, especially for the prevention or treatment of a bacterial infection, in particular for the prevention or treatment of a bacterial infection caused by Gram-negative bacteria (notably for the prevention or treatment of a bacterial infection caused by *Escherichia coli* bacteria, *Klebsiella pneumoniae* bacteria or *Pseudomonas aeruginosa* bacteria, and in particular for the prevention or treatment of a bacterial infection caused by *Klebsiella pneumoniae* quinolone-resistant, carbapenem-resistant or multi-drug resistant bacteria). The following embodiments relating to the compounds of formula I according to embodiment 1) are thus possible and intended and herewith specifically disclosed in individualised form:

1, 2+1, 3+2+1, 4+1, 4+2+1, 5+4+1, 5+4+2+1, 6+5+4+1, 6+5+4+2+1, 7+5+4+1, 7+5+4+2+1, 8+4+1, 8+4+2+1, 9+8+4+1, 9+8+4+2+1, 10+1, 10+2+1, 11+10+1, 11+10+2+1, 12+11+10+1, 12+11+10+2+1, 13+10+1, 13+10+2+1, 14+1, 14+2+1, 15+14+1, 15+14+2+1, 16+15+14+1, 16+15+14+2+1, 17+14+1, 17+14+2+1, 18+1, 19+1, 20+1, 20+2+1, 20+3+2+1, 20+4+1, 20+4+2+1, 20+5+4+1, 20+5+4+2+1, 20+6+5+4+1, 20+6+5+4+2+1, 20+7+5+4+1, 20+7+5+4+2+1,

20+8+4+1, 20+8+4+2+1, 20+9+8+4+1, 20+9+8+4+2+1, 20+10+1, 20+10+2+1, 20+11+10+1, 20+11+10+2+1, 20+12+11+10+1, 20+12+11+10+2+1, 20+13+10+1, 20+13+10+2+1, 20+14+1, 20+14+2+1, 20+15+14+1, 20+15+14+2+1, 20+16+15+14+1, 20+16+15+14+2+1, 20+17+14+1, 20+17+14+2+1, 20+18+1, 20+19+1, 21+1, 21+2+1, 22+4+1, 22+4+2+1, 22+5+4+1, 22+5+4+2+1, 22+6+5+4+1, 22+6+5+4+2+1, 22+7+5+4+1, 22+7+5+4+2+1, 22+8+4+1, 22+8+4+2+1, 22+9+8+4+1, 22+9+8+4+2+1, 22+10+1, 22+10+2+1, 22+11+10+1, 22+11+10+2+1, 22+12+11+10+1, 22+12+11+10+2+1, 22+13+10+1, 22+13+10+2+1, 22+14+1, 22+14+2+1, 22+15+14+1, 22+15+14+2+1, 22+16+15+14+1, 22+16+15+14+2+1, 22+17+14+1, 22+17+14+2+1, 22+18+1, 22+19+1.

In the list above, the numbers refer to the embodiments according to their numbering provided hereinabove whereas "+" indicates the dependency from another embodiment. The different individualised embodiments are separated by commas. In other words, "4+2+1" for example refers to embodiment 4) depending on embodiment 2), depending on embodiment 1), i.e. embodiment "4+2+1" corresponds to embodiment 1) further limited by the features of embodiments 2) and 4). Likewise, "9+8+4+1" refers to embodiment 9) depending mutatis mutandis on embodiments 8) and 4), depending on embodiment 1), i.e. embodiment "9+8+4+1" corresponds to embodiment 1) further limited by the features of embodiments 4) and 8), further limited by the features of embodiment 9).

The compounds of formula I can be manufactured in accordance with the present invention using the procedures described hereafter.

PREPARATION OF THE COMPOUNDS OF FORMULA I

Abbreviations

The following abbreviations are used throughout the specification and the examples:
Ac acetyl
AcOH acetic acid
aq. aqueous
Bz benzoyl
CC column chromatography over silica gel
CDI 1,1'-carbonyldiimidazole
Cipro ciprofloxacin
DAD diode array detection
DCC dicyclohexylcarbodiimide
DCE 1,2-dichloroethane
DCM dichloromethane
DIPEA N,N-diisopropylethylamine
DMF N,N-dimethylformamide
DMSO dimethylsulfoxide
EA ethyl acetate
EDC N-(3-dimethylaminopropyl)-N'-ethylcarbodiimide hydrochloride
ELSD evaporative light scattering detector
ESI electron spray ionisation
Et ethyl
Et$_2$O diethyl ether
EtOH ethanol
HATU O-(7-azabenzotriazol-1-yl)-N,N,N',N'-tetramethyl-uronium hexafluorophosphate
Hept heptane
Hex hexane
HOBT hydroxybenzotriazole
HPLC high pressure liquid chromatography
iPr iso-propyl
iPrOH iso-propanol
IT internal temperature
LC liquid chromatography
MCPBA meta-chloro perbenzoic acid
Me methyl
MeCN acetonitrile
MeOH methanol
MS mass spectroscopy
NBS N-bromosuccinimide
NMR Nuclear Magnetic Resonance
org. organic
Pd/C palladium on carbon
Ph phenyl
PPTS para-toluenesulfonic acid pyridinium salt
prep-HPLC preparative HPLC
Pyr pyridine
quant. quantitative yield
rt room temperature
sat. saturated
T3P propylphosphonic anhydride
TBAF tetra-n-butylammonium fluoride
TBME tert-butyl methyl ether
tBu tert-butyl
tBuOH tert-butanol
TEA triethylamine
TFA trifluoroacetic acid
THF tetrahydrofuran
THP tetrahydropyranyl
TLC thin layer chromatography
TMSE 2-(trimethylsilyl)ethyl
t$_R$ retention time
General Reaction Techniques:
General Reaction Technique 1 (Protecting Group Removal):

The protecting groups of hydroxamic acid ester derivatives (CONHOPG), the protecting groups of phosphonic acid ester derivatives (P(O)(OPG')$_2$ and the protecting groups of alcohol derivatives (OPG") are removed as follows:

When PG, PG' or PG" is THP, (2-methylpropoxy)ethyl, methoxymethyl, tBu, COOtBu or COtBu: by acidic treatment with e.g. TFA or HCl in an org. solvent such as DCM, dioxane, Et$_2$O or MeOH between 0° C. and rt or by treatment with pyridinium para-toluenesulfonate in EtOH between rt and about +80° C.;

When PG, PG' or PG" is trityl: by treatment with diluted acid such as citric acid or HCl in an org. solvent such as MeOH or DCM;

When PG, PG' or PG" is TMSE: by using fluoride anion sources such as BF$_3$.etherate complex in MeCN at 0° C., TBAF in THF between 0° C. and about +40° C. or HF in MeCN or water between 0° C. and +40° C., or using acidic conditions such as AcOH in THF/MeOH or HCl in MeOH;

When PG, PG' or PG" is allyl: by treatment with Pd(PPh$_3$)$_4$ in a solvent such as MeOH in presence of K$_2$CO$_3$ or a scavenger such as dimedone, morpholine or tributyltin hydride;

When PG" is TBDPS or TBDMS: by using fluoride anion sources such TBAF in THF between 0° C. and +40° C. or HF in MeCN or water between 0° C. and +40° C., or using acidic conditions such as TFA in DCM;

When PG" is Ac or Bz: by treatment with an inorganic base such as K$_2$CO$_3$ in a solvent such as MeOH between 0° C. and about +40° C.; or by treatment with an alkali hydroxide such as LiOH, KOH or NaOH in a water-dioxane or water-THF mixture between 0° C. and +80° C.

Further general methods to remove hydroxamic acid protecting groups have been described in T. W. Greene & P. G. M. Wuts, *Protecting Groups in Organic Synthesis*, 3$^{rd}$ Ed (1999), 23-147 (Publisher: John Wiley and Sons, Inc., New York, N.Y.).

General Reaction Technique 2. (Peptide-Type Coupling):

The carboxylic acid is reacted respectively with the hydroxylamine derivative or an hydroxamic acid in the presence of an activating agent such as DCC, EDC, HOBT, n-propylphosphonic cyclic anhydride, HATU or di-(N-succinimidyl)-carbonate, in a dry aprotic solvent such as DCM, MeCN or DMF between −20° C. and about +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and about +60° C. Further activating agents can be found in R. C. Larock, *Comprehensive Organic Transformations. A guide to Functional Group Preparations*, 2$^{nd}$ Edition (1999), section nitriles, carboxylic acids and derivatives, p. 1941-1949 (Wiley-VC; New York, Chichester, Weinheim, Brisbane, Singapore, Toronto).

General Reaction Technique 3 (Alkyne-Alkyne Cross Coupling, Haloaryl-Alkyne or Alkyne-Haloalkyne Cross Coupling):

An alkyne derivative is coupled with a second alkyne, an haloaryl such as a bromo- or an iodoaryl, or a haloalkyne derivative, using a catalytic amount of a palladium salt, an org. base such as TEA and a catalytic amount of a copper derivative (usually copper iodide) in a solvent such as DMF at a temperature from 20 to 100° C. (see Sonogashira, K. in *Metal-Catalyzed Reactions*, Diederich, F., Stang, P. J., Eds.; Wiley-VCH: New York (1998)). Alternatively, the alkyne-haloalkyne cross coupling reaction can be performed using only a catalytic amount of copper derivative in the presence of aqueous hydroxylamine and a base such as piperidine or pyrrolidine (see Chodkiewicz and Cadiot, C. R. *Hebd. Seances Acad. Sci.* (1955), 241, 1055-1057).

General Reaction Technique 4 (Transformation of an Ester into an Acid):

When the ester side chain is a linear alkyl, the hydrolysis is usually performed by treatment with an alkali hydroxide such as LiOH, KOH or NaOH in a water-dioxan or water-THF mixture between 0° C. and 80° C. When the ester side chain is tBu, the release of the corresponding acid can also be performed in neat TFA or diluted TFA or HCl in an org. solvent such as ether or THF. When the ester side chain is the allyl group, the reaction is performed in the presence of tetrakis(triphenylphosphine)palladium(0) in the presence of an allyl cation scavenger such as morpholine, dimedone or tributyltin hydride between 0° C. and 50° C. in a solvent such as THF. When the ester side chain is benzyl, the reaction is performed under hydrogen in the presence of a noble metal catalyst such as Pd/C in a solvent such as MeOH, THF or EA. Further strategies to introduce other acid protecting groups and general methods to remove them have been described in T. W. Greene & P. G. M. Wuts, *Protecting Groups in Organic Synthesis*, 3$^{rd}$ Ed. (1999), 369-441 (Publisher: John Wiley and Sons, Inc., New York, N.Y.).

General Reaction Technique 5 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBHCN$_3$, or NaBH(OAc)$_3$ or through hydrogenation over a noble metal catalyst such as Pd/C. The reaction is carried out between about −10° C. and about +110° C., preferably between 0° C. and 60° C. The reaction can also be carried out in one pot. It can also be performed in protic solvents such as MeOH or water in presence of a picoline-borane complex (Sato et al., *Tetrahedron* (2004), 60, 7899-7906).

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The sections hereafter describe general methods for preparing compounds of formula I. If not indicated otherwise, the generic groups $R^1$, $R^2$, M, $M^A$, $M^B$, $M^C$, $L^1$, $L^{2A}$, $L^{2BC}$, $R^{1A}$, $R^{2A}$ and $R^{2BC}$ are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example T. W. Greene and P. G. M. Wuts, *Protective Groups in Organic Synthesis*, 3$^{rd}$ Ed. (1999), Wiley-Interscience).

The compounds of formula I wherein $R^1$ is H can be obtained by deprotecting a compound of formula II

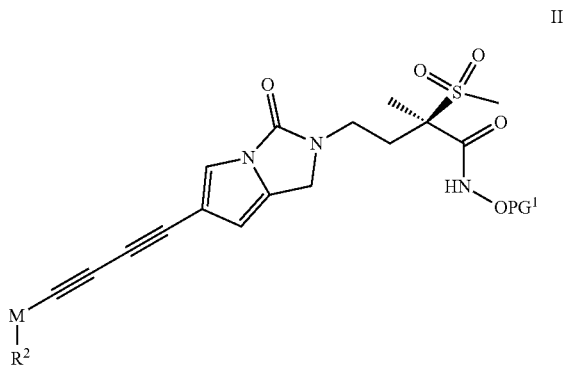

II wherein M is as defined in formula I and $R^2$ has the same meaning as in formula I when $R^1$ represents H (whereby functional groups of $R^2$ may possibly be present in a protected form) and PG$^1$ represents THP, TMSE, trityl, (2-methylpropoxy)ethyl, methoxymethyl, allyl, tBu, COOtBu or COtBu using general reaction technique 1. Protecting groups possibly present on $R^2$ can be deprotected before or concomitantly to said reaction. The reaction can also be performed with racemic material and the (R)-enantiomer can be obtained by chiral HPLC separation.

The compounds of formula I wherein $R^2$ is H can be obtained by:
i) reacting a compound of formula III

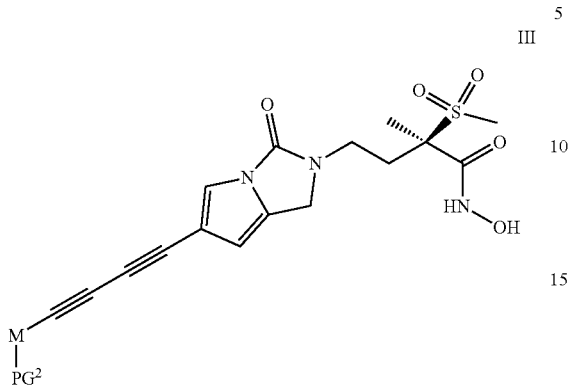

wherein M is as defined in formula I and $PG^2$ represents Ac, Bz, THP, TBDPS, TBDMS or methoxymethyl, with a compound of formula IV $(PG^4O)_2P—N-(iPr)_2$      IV wherein $PG^4$ represents tert-butyl, the reaction being performed in the presence of a base such as tetrazole in a solvent such as acetonitrile at a temperature in the vicinity of 0° C. and an oxidation reaction being subsequently performed adding an oxidizing agent such as hydrogen peroxide in water or MCPBA (this reaction sequence can also be performed with racemic compound of formula III and the (R)-enantiomer can then be obtained by chiral HPLC separation of the reaction products), whereby cleavage of $PG^4$ and $PG^2$ can be performed concomitantly or sequentially using general reaction technique 1, yielding compounds of formula I wherein $R^1$ is $PO_3H_2$; or ii) reacting a compound of formula III as defined in section a) above with a compound of formula V $HO(O)CR^{1.4}$      V wherein $R^{1.4}$ has the same meaning as in formula I, the reaction being performed using general reaction technique 2 and subsequent cleavage of $PG^2$ being performed using general reaction technique 1 (this reaction sequence can also be performed with racemic compound of formula III and the (R)-enantiomer can then be obtained by chiral HPLC separation of the reaction products), whereby functional groups (e.g. amino or hydroxy) present on $R^{1.4}$ that would be incompatible with the abovementioned reaction conditions can be protected before performing said reaction and deprotected after performing said reaction, yielding compounds of formula I wherein $R^1$ is $C(O)R^{1.4}$; or iii) reacting a compound of formula III as defined in section a) above with a compound of formula VI $X^a—(CH_2)—O—P(O)(OPG^4)_2$      VI wherein $X^a$ represents iodine, bromine or chlorine and $PG^4$ has the same meaning as in formula IV, the reaction being performed in the presence of a mineral base such as NaH or $K_2CO_3$ or in the presence of an organic base such as TEA or DIPEA in a solvent such as THF at a temperature ranging between about −50° C. and rt and the subsequent cleavage of $PG^4$ and $PG^2$ being performed concomitantly or sequentially using general reaction technique 1 (this reaction sequence can also be performed with racemic compound of formula III and the (R)-enantiomer can then be obtained by chiral HPLC separation of the reaction products), yielding compounds of formula I wherein $R^1$ is $CH_2—O—PO_3H_2$; or iv) reacting a compound of formula III as defined in section a) above with $Pyr.SO_3$ complex or $Me_2NCHO.SO_3$ complex in a solvent such as DMF or Pyr and subsequently cleaving $PG^2$ using general reaction technique 1 (this reaction sequence can also be performed with racemic compound of formula III and the (R)-enantiomer can then be obtained by chiral HPLC separation of the reaction products), yielding compounds of formula I wherein $R^1$ is $SO_3H$.

If desired, the compounds of formula I thus obtained may be converted into their salts, and notably into their pharmaceutically acceptable salts using standard methods.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in the presence or absence of an amine such as TEA or diethylamine) and eluent B (Hex), at a flow rate of 0.8 to 150 mL/min.

Preparation of the Compounds of Formula II.

The compounds of formula II can be obtained by:
a) reacting a compound of formula VII

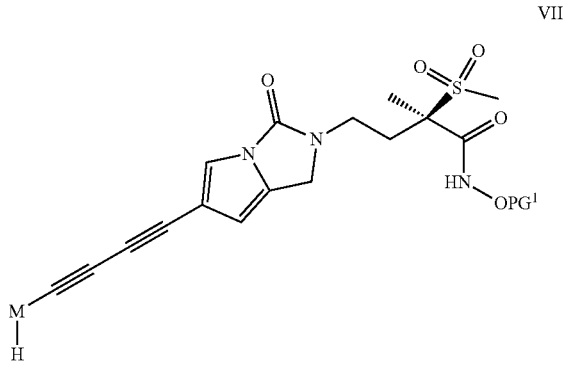

wherein M and $PG^1$ are as defined in formula II with a compound of formula IV $(PG^4O)_2P—N-(iPr)_2$      IV wherein $PG^4$ represents tert-butyl, the reaction being performed in the presence of a base such as tetrazole in a solvent such as acetonitrile at a temperature in the vicinity of 0° C. and an oxidation reaction being subsequently performed adding an oxidizing agent such as hydrogen peroxide in water or MCPBA (this reaction sequence can also be performed with racemic compound of formula VII and the (R)-enantiomer can then be obtained by chiral HPLC separation of the reaction products), whereby cleavage of $PG^4$ can then be performed using general reaction technique 1 and under said conditions concomitant cleavage of $PG^1$ can occur, yielding in the latter case directly the compounds of formula I wherein $R^2$ is $PO_3H_2$; or b) reacting a compound of formula VII as defined in section a) above with a compound of formula Va or of formula Vb HO(O)CR$^{2A}$      Va HO(O)CR$^{2BC}$      Vb wherein R$^{2A}$ and R$^{2BC}$ are as defined in formula I, which reaction can be performed using general reaction technique 2 (this reaction can also be performed with racemic compound of formula VII and the (R)-enantiomer can then be obtained by chiral HPLC separation of the reaction products), whereby functional groups (e.g. amino or hydroxy) present on R$^{2A}$ and R$^{2BC}$ that would be incompatible with the above-mentioned reaction conditions can be protected before performing said reaction and deprotected after performing said reaction, yielding compounds of formula II wherein R$^2$ is (O)CR$^{2A}$ or (O)CR$^{2BC}$; or c) reacting a compound of formula VII as defined in section a) above with a compound of formula VI X$^a$—(CH$_2$)—O—P(O)(OPG$^4$)$_2$      VI wherein X$^a$ represents iodine, bromine or chlorine and PG$^A$ is as defined in formula IV, the reaction being performed in the presence of a mineral base such as NaH or K$_2$CO$_3$ or in the presence of an organic base such as TEA or DIPEA in a solvent such as THF at a temperature ranging between −50° C. and rt and subsequent cleavage of PG$^A$ being performed using general reaction technique 1 (this reaction sequence can also be performed with racemic compound of formula VII and the (R)-enantiomer can then be obtained by chiral HPLC separation of the reaction products), whereby under said conditions concomitant cleavage of PG$^1$ can occur, yielding in the latter case directly compounds of formula I wherein R$^2$ is CH$_2$—O—PO$_3$H$_2$; or d) reacting a compound of formula VII as defined in section a) above with Pyr.SO$_3$ complex or Me$_2$NCHO.SO$_3$ complex in a solvent such as DMF or Pyr (this reaction can also be performed with racemic compound of formula VII and the (R)-enantiomer can then be obtained by chiral HPLC separation of the reaction products); or e) reacting a compound of formula VIII

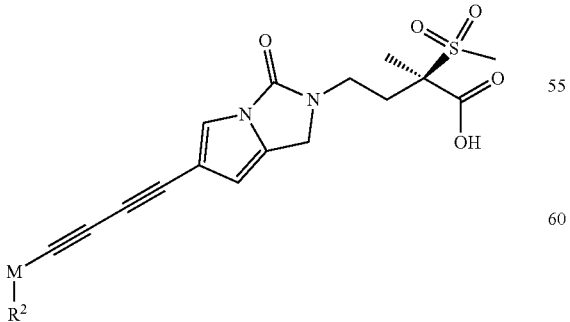

VIII wherein M and R$^2$ are as defined in formula I with a compound of formula IX

H$_2$N—OPG$^1$      IX wherein PG$^1$ has the same meaning as in formula II using general reaction technique 2 (this reaction can also be performed with racemic compound of formula VIII and the (R)-enantiomer can then be obtained by chiral HPLC separation of the reaction products), whereby functional groups present on R$^2$ that would be incompatible with the coupling conditions mentioned in general reaction technique 2 can be protected before performing said reaction and then deprotected before or concomitantly to PG$^1$ (leading in this latter instance to a compound of formula I); or f) reacting a compound of formula X

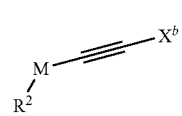

X wherein M is as defined in formula I, R$^2$ has the same meaning as in formula I when R$^1$ represents H and X$^b$ represents bromine or iodine, with a compound of formula XI

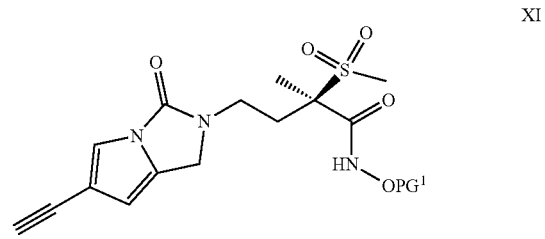

XI wherein PG$^1$ has the same meaning as in formula II, using general reaction technique 3 (this reaction can also be performed with racemic compound of formula X and/or racemic compound of formula XI and the (R)-enantiomer or (R)-configured diastereomers can then be obtained by chiral HPLC separation of the reaction products), whereby functional groups present on R$^2$ that would be incompatible with the coupling conditions mentioned in general reaction technique 3 can be protected before performing said reaction and then deprotected before or concomitantly to PG$^1$ (leading in this latter instance to a compound of formula I).

Preparation of the Synthesis Intermediates of Formulae III, IV, Va, Vb, VI, VII, VIII, IX, X and XI:

Compounds of Formulae III and VII:

The compounds of formulae III and VII can be prepared as summarised in Scheme 1 hereafter.

Scheme 1

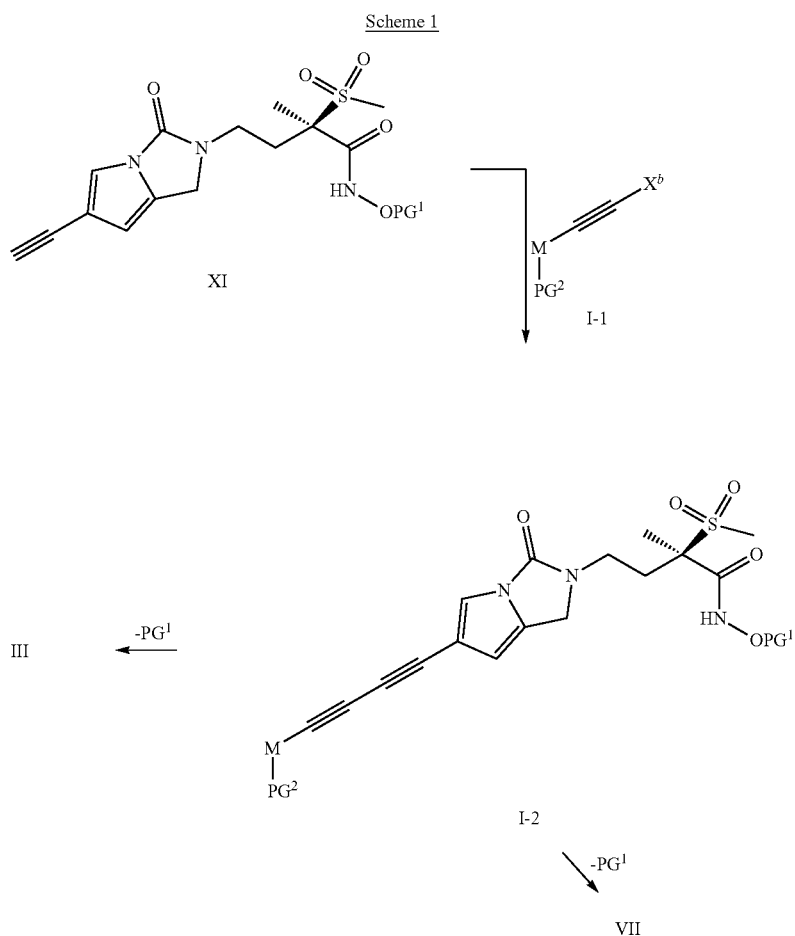

In Scheme 1, M and PG$^1$ have the same meaning as in formula II, PG$^2$ has the same meaning as in formula III, provided that PG$^1$ and PG$^2$ belong to orthogonal sets of protecting groups, and X$^b$ is bromine or iodine.

The derivatives of formula I-2 can be obtained (Scheme 1) from the compounds of formula XI and the compounds of formula I-1 applying general reaction technique 3. This reaction can also be performed with racemic compounds of formula XI or I-1 and the (R)-enantiomer or (R)-configured diastereomers can then be obtained by chiral HPLC separation of the reaction products. Selective cleavage of PG$^1$, using a reaction of general reaction technique 1 that is not going to cleave PG$^2$, leads to compounds of formula III. Conversely, selective cleavage of PG$^2$, using a reaction of general reaction technique 1 that is not going to cleave PG$^1$, leads to compounds of formula VII.

An alternative method for preparing the compounds of formula I-2 of Scheme 1, and thus the compounds of formulae III and VII after selective cleavage of PG$^1$ or PG$^2$ as described previously, is summarised in Scheme 2 hereafter.

Scheme 2

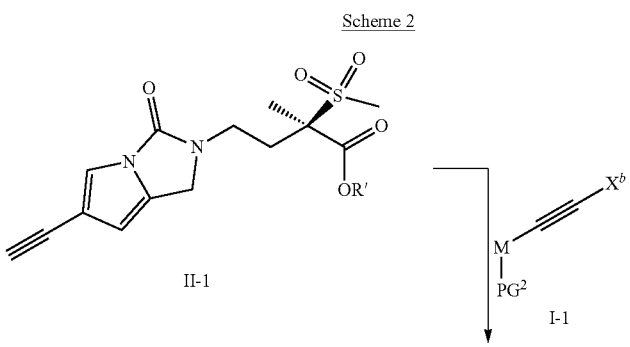

-continued

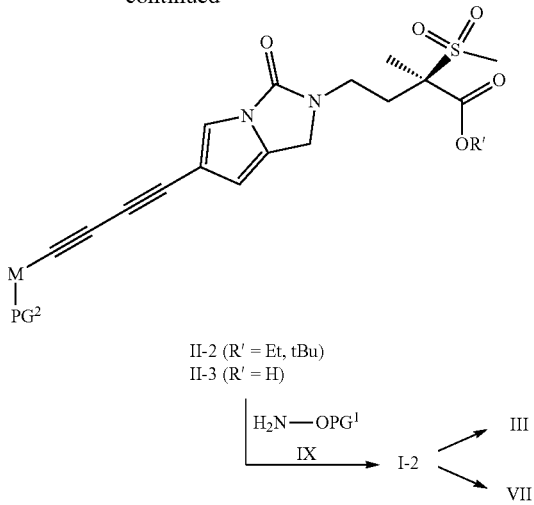

II-2 (R' = Et, tBu)
II-3 (R' = H)

$$\xrightarrow[\text{IX}]{\text{H}_2\text{N——OPG}^1} \text{I-2} \begin{array}{c} \nearrow \text{III} \\ \searrow \text{VII} \end{array}$$

In Scheme 2, M and $PG^1$ have the same respective meanings as in formula II, R' is H, Et or tBu, $PG^2$ has the same meaning as in formula III, provided that $PG^1$ and $PG^2$ belong to orthogonal sets of protecting groups and $X^b$ is bromine or iodine.

The derivatives of formula II-2 wherein R' is Et or tBu can be obtained (Scheme 2) from the compounds of formula II-1 wherein R' is Et or tBu and the compounds of formula I-1 applying general reaction technique 3. This reaction can also be performed with racemic compounds of formula II-1 and/or I-1 and the (R)-enantiomer or (R)-configurated diastereomers can then be obtained by chiral HPLC separation of the reaction products. Compounds of formula II-2 can be transformed to compound of formula II-3 wherein R' is H by selective cleavage of Et or tBu, using one of the general reaction technique 4 that is not going to cleave $PG^2$. The compounds of formula II-3 can be transformed to the compounds of formula I-2 using compounds of formula IX and general reaction technique 2. Finally the compounds of formulae III and VII can be obtained from the compounds of formula I-2 after selective cleavage of $PG^1$ or $PG^2$ as described previously.

The compounds of formula VII can moreover be obtained as summarised in Scheme 3 hereafter.

Scheme 3

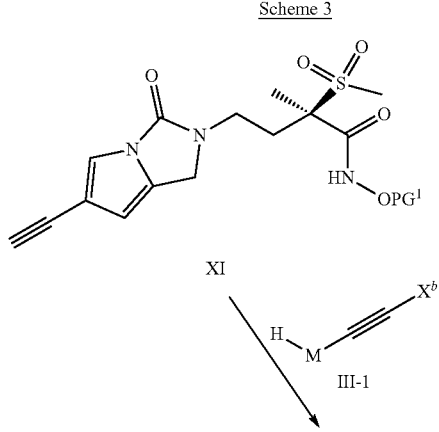

-continued

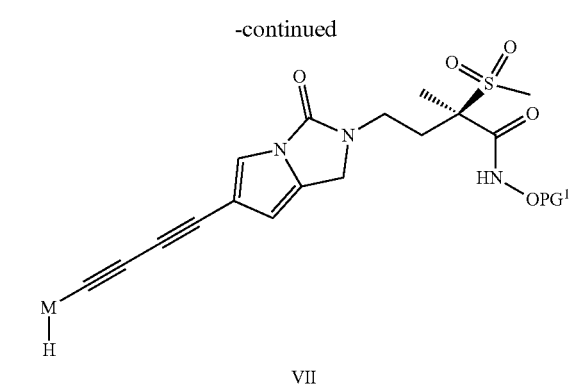

VII

In Scheme 3, M has the same meaning as in formula I and $X^b$ is bromine or iodine.

The derivatives of formula VII can be obtained (Scheme 3) from the compounds of formula XI and the compounds of formula III-1 applying general reaction technique 3. This reaction can also be performed with racemic compounds of formulae XI and/or III-1 and the (R)-enantiomer or (R)-configurated diastereomers can then be obtained by chiral HPLC separation of the reaction products.

Compounds of Formulae IV, V, Va, Vb and VI.

The compounds of formulae IV, V, Va, Vb and VI are commercially available or can be prepared by standard methods known to one skilled in the art.

Compounds of Formula VIII:

The compounds of formula VIII can be obtained as summarised in Scheme 4 hereafter.

Scheme 4

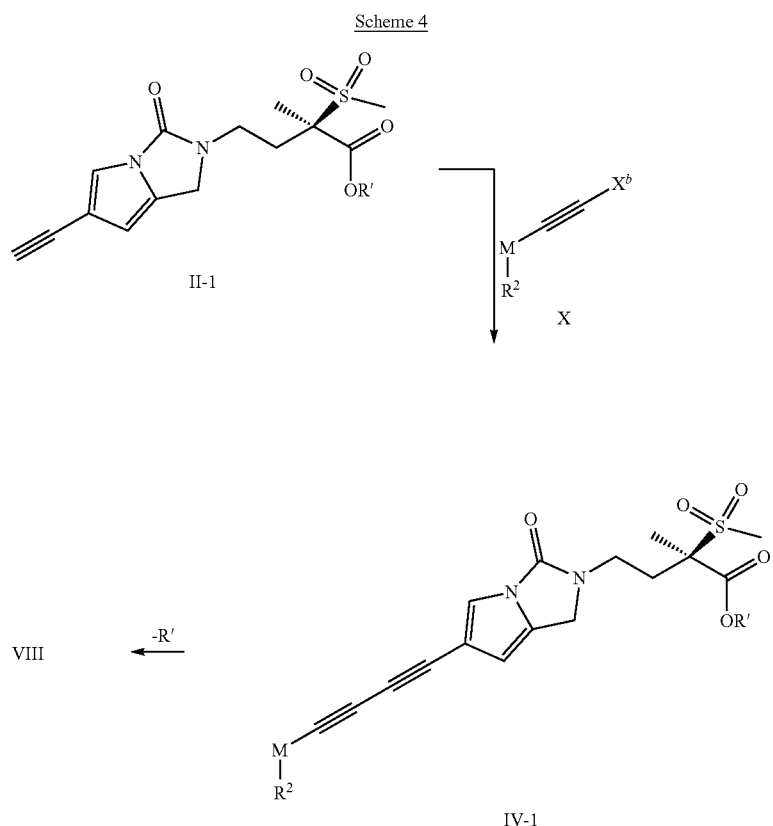

In Scheme 4, M is as defined in formula I, $R^2$ have the same meaning as in formula I when $R^1$ represents H, R' is Et or tBu and $X^b$ is bromine or iodine.

The derivatives of formula IV-1 wherein can be obtained (Scheme 4) from the compounds of formula II-1 and the compounds of formula X using general reaction technique 3. This reaction can also be performed with racemic compounds of formulae II-I and/or X and the (R)-enantiomer or (R)-configurated diastereomers can then be obtained by chiral HPLC separation of the reaction products. Functional groups present on $R^2$ that would be incompatible with the coupling conditions mentioned in general reaction technique 3 can be protected before performing said reaction and deprotected after said reaction if necessary. The compounds of formula IV-1 can then be transformed into compounds of formula VIII by selective cleavage of R', using a suitable method from general reaction technique 4.

Compounds of Formula IX

The compounds of formula IX are commercially available ($PG^1$=THP, tBu, COOtBu or allyl) or can be prepared according to WO 2010/060785 ($PG^1$=(2-methylpropoxy)ethyl) or Marmer and Maerker, J. Org. Chem. (1972), 37, 3520-3523 (PG=COtBu).

Compounds of Formula X:

The compounds of formula X can be obtained as summarised in Scheme 5 hereafter.

Scheme 5

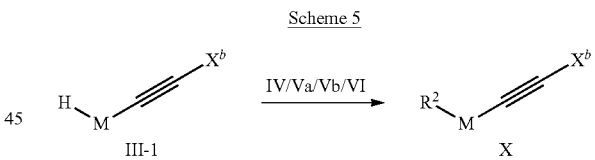

In Scheme 5, M is as defined in formula I, $R^2$ has the same meaning as in formula I when $R^1$ represents H and $X^b$ is bromine or iodine.

The compounds of formula III-1 can be transformed (Scheme 5) into the derivatives of formula X using the corresponding methods described above for the preparation of the compounds of formula II [sections a) to c)].

Besides, the compounds of formulae III-1 and X wherein $X^b$ represents iodine can be prepared by iodination of the corresponding hydrogen derivatives with iodine in the presence of an inorganic base such as KOH. The compounds of formulae III-1 and X wherein $X^b$ represents bromine can be prepared from the corresponding hydrogen derivatives by treatment with NBS in the presence of $AgNO_3$ in a solvent such as acetone or MeCN.

Compounds of Formula XI:

The compounds of formula XI can be prepared as summarised in Scheme 6 hereafter.

Scheme 6

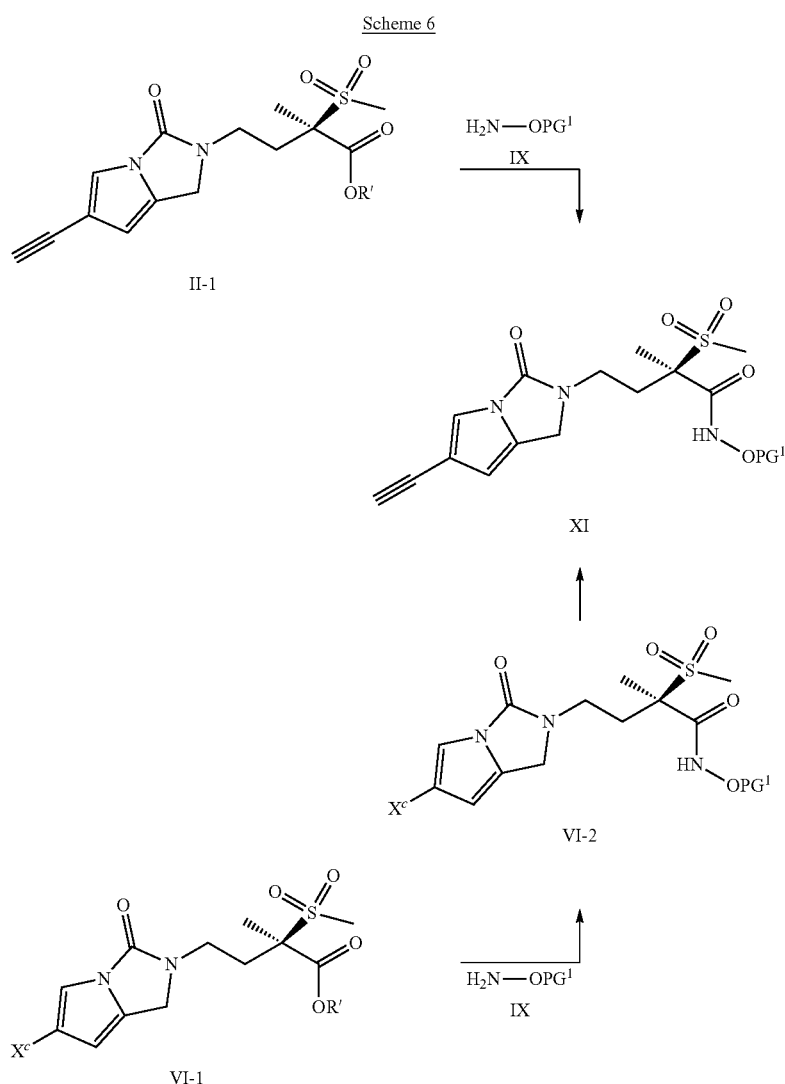

In Scheme 6, R' represents H, Et or tBu, $X^c$ represents a bromine or iodine atom and $PG^1$ has the same meaning as in formula II.

The derivatives of formula II-1 wherein R' is Et or tBu can be transformed (Scheme 5) into the carboxylic acid derivatives of formula II-1 wherein R' is H using general reaction technique 4 and further reacted with the compounds of formula IX using general reaction technique 2, thus affording the compounds of formula XI. Alternatively, the derivatives of formula VI-1 wherein R' is Et or tBu can be transformed into the carboxylic acid derivatives of formula VI-1 wherein R' is H using general reaction technique 4 and further reacted with the compounds of formula IX using general reaction technique 2, thus affording the compounds of formulae VI-2. The compounds of formulae VI-1 and VI-2 wherein $X^c$ is Br can be transformed to the corresponding compounds of formulae VI-1 and VI-2 wherein $X^c$ is I by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at about 150° C. The compounds of formula XI can be obtained by reaction of the compounds of formula VI-2 wherein $X^c$ is iodine with trimethylsilylacetylene using general reaction technique 3 followed by treatment with TBAF in THF. All these reactions can also be performed with racemic material and the suitable enantiomer can be obtained by chiral HPLC separation at any step when appropriate.

Other Synthesis Intermediates and Starting Materials:

The compounds of formula I-1 can be prepared as summarised in Scheme 7 hereafter.

Scheme 7

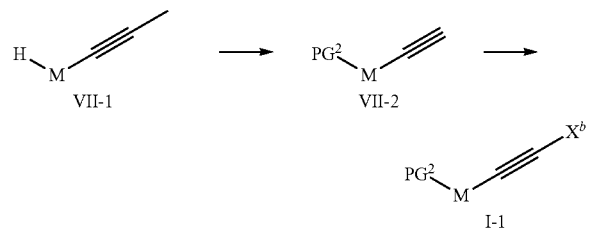

In Scheme 7, M and PG² have the same respective meanings as in formula III and X^b represents a bromine or iodine atom.

The compounds of formula VII-1 (which are commercially available or can be prepared by standard methods known to one skilled in the art) can be transformed (Scheme 7) into the derivatives of formula VII-2 using above methods described in T. W. Greene & P. G. M. Wuts, *Protecting Groups in Organic Synthesis*, 3^rd Ed. (1999), 369-441 (Publisher: John Wiley and Sons, Inc., New York, N.Y.). The compounds of formula I-1 wherein X^b represents iodine can be prepared by iodination of compounds of formula VII-2 with iodine in the presence of an inorganic base such as KOH. The compounds of formula I-1 wherein X^b represents bromine can be prepared from the compounds of formula VII-2 by treatment with NBS in the presence of AgNO₃ in a solvent such as acetone or MeCN. All these reactions can also be performed with racemic material and the suitable enantiomer can be obtained by chiral HPLC separation at any step when appropriate.

The compounds of formulae II-1 and VI-1 wherein R' is tBu can be prepared as summarised in Scheme 8 hereafter.

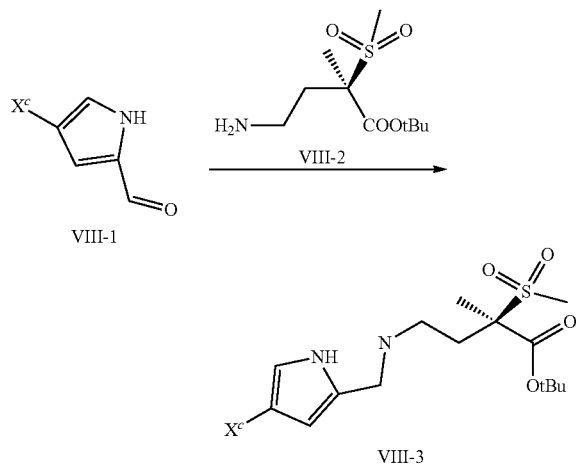

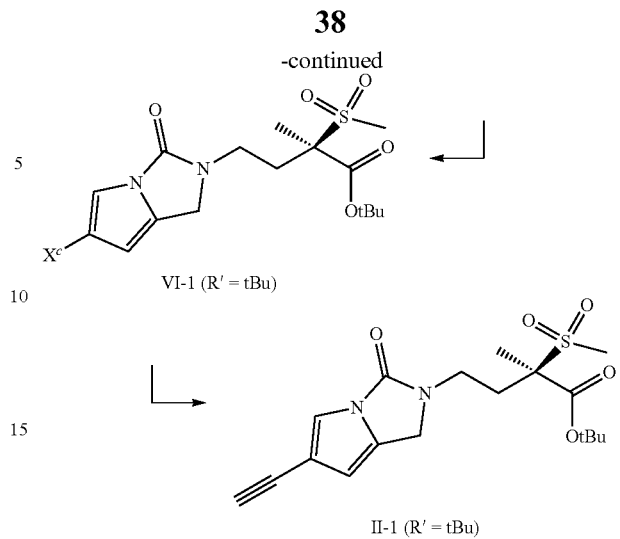

In Scheme 8, X^c represents a bromine or iodine atom.

The derivative of formula VIII-3 can be obtained (Scheme 8) by reaction of the pyrrole aldehyde of formula VIII-1 with the amine of formula VIII-2 using general reaction technique 5. The compound of formula VI-1 wherein R' is tBu can then be obtained from the derivative of formula VIII-3 by treatment with CDI in the presence of a base such as NaH in a solvent such as THF; this reaction can be performed at a temperature ranging from 0° C. to 50° C., and ideally at rt. The compound of formula VI-1 wherein X^c is Br and R' is tBu can be transformed into the corresponding compound of formula VI-1 wherein X^c is I and R' is tBu by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at about 150° C. The compound of formula VI-1 wherein X^c is I can be transformed to the derivative of formula II-1 wherein R' is tBu by reaction with trimethylsilylacetylene using general reaction technique 4 followed by treatment with TBAF in THF. All these reactions can also be performed with racemic material and the suitable enantiomer can be obtained by chiral HPLC separation at any step when appropriate.

The compounds of formulae II-1 and VI-1 wherein R' is Et can be prepared as summarised in Scheme 9 hereafter.

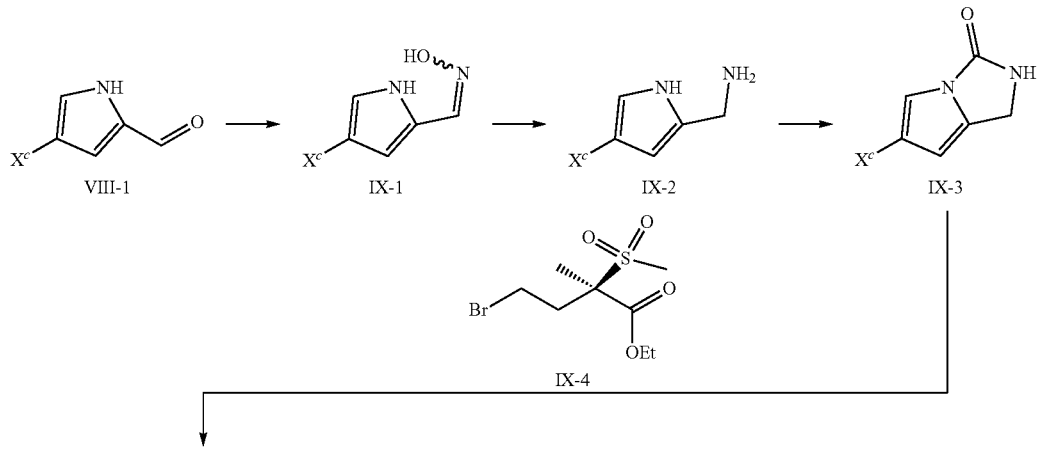

-continued

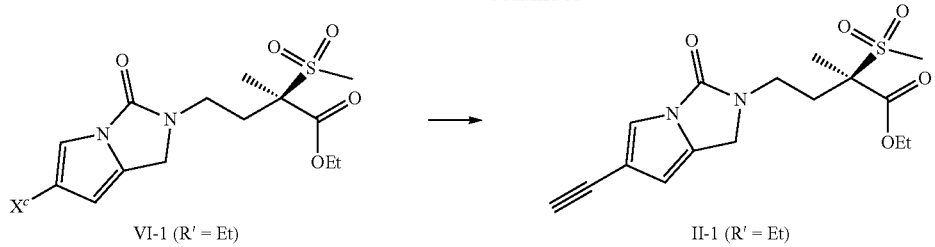

VI-1 (R' = Et) → II-1 (R' = Et)

In Scheme 9, $X^c$ represents a bromine or iodine atom.

The oxime of formula IX-1 can be obtained (Scheme 9) by reaction of the pyrrole aldehyde of formula VIII-1 with hydroxylamine in AcOH in the presence of NaOAc. The oxime of formula IX-1 can be reduced into the amine derivative of formula IX-2 by treatment with Zn in a solvent such as AcOH. The derivative of formula IX-3 can be obtained from the derivative of formula IX-2 by treatment with CDI in a solvent such as THF in the presence of a base such as NaH; this reaction can be performed at a temperature ranging from 0 to 50° C., and ideally at rt. The compound of formula IX-3 can then be transformed into the compound of formula VI-1 wherein R' is Et by treatment with the bromide of formula IX-4 in the presence of a base such as NaH and in a solvent such as THF or DMF. The compound of formula VI-1 wherein $X^c$ is Br and R' is Et can be transformed to the corresponding compound of formula VI-1 wherein $X^c$ is I and R' is Et by reaction with NaI in the presence of a copper (I) salt and a ligand such as trans-N,N'-dimethylcyclohexa-1,2-diamine in a solvent such as dioxane at a temperature ranging between rt and 100° C., or in a microwave oven at about 150° C. The compound of formula VI-1 wherein $X^c$ is iodine can be transformed to the compound of formula II-1 wherein R' is Et by reaction with trimethylsilylacetylene using general reaction technique 4 followed by treatment with TBAF in THF.

The compounds of formula VII-1 and VIII-1 are commercially available or can be prepared by standard methods known to one skilled in the art.

The compounds of formulae VIII-2 and IX-4 can be prepared in analogy to the methods described in the section entitled "EXAMPLES" hereafter (see Preparations A and B), or by standard methods known to one skilled in the art.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt. The combined org layers resulting from the workup of an aq. layer are, unless otherwise indicated, washed with a minimal volume of brine, dried over $MgSO_4$, filtered and evaporated to dryness to leave a so-called evaporation residue.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60 A silica gel (0.032-0.63 mm) or using an ISCO CombiFlash system and prepacked $SiO_2$ cartridges, elution being carried out with either Hept-EA or DCM-MeOH mixtures with an appropriate gradient. When the compounds contained an acid function, 1% of AcOH was added to the eluent(s). When the compounds contained a basic function, 25% aq. $NH_4OH$ was added to the eluents.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
  Column: Zorbax SB-Aq, 30.5 µm, 4.6×50 mm;
  Injection volume: 1 µL;
  Column oven temperature: 40° C.;
  Detection: UV 210 nm, ELSD and MS;
  MS ionization mode: ESI+;
  Eluents: A: $H_2O$+0.04% TFA; and B: MeCN;
  Flow rate: 40.5 mL/min;
  Gradient: 5% B to 95% B (0.0 min-1.0 min), 95% B (1.0 min-1.45 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
  Method 1:
    Column: Waters Atlantis T3 OBD, 10 µm, 30×75 mm;
    Flow rate: 75 mL/min;
    Eluents: A: $H_2O$+0.1% HCOOH; B: MeCN+0.1% HCOOH;
    Gradient: 90% A to 5% A (0.0 min-4.0 min), 5% A (4.0 min-6.0 min).
  Method 2:
    Column: Waters XBridge C18, 10 µm, 30×75 mm;
    Flow rate: 75 mL/min;
    Eluents: A: $H_2O$+0.5% HCOOH; B: MeCN;
    Gradient: 90% A to 5% A (0.0 min-4.0 min), 5% A (4.0 min-6.0 min).
  Method 3:
    Column: Waters XBridge C18, 10 µm, 30×75 mm;
    Flow rate: 75 mL/min;
    Eluents: A: $H_2O$+25% aq. $NH_4OH$ (0.5% v/v); B: MeCN;

Gradient: 90% A to 5% A (0.0 min-4.0 min), 5% A (4.0 min-6.0 min).

Besides, semi-preparative chiral HPLCs were performed using the conditions herafter.

Semi-Preparative Chiral HPLC Method A:

The semi-preparative chiral HPLC is performed on a Daicel ChiralPak ASV column (250×110 mm, 20 μm) using the eluent mixture, flow rate and detection conditions indicated between brackets in the corresponding experimental protocol. The retention times are obtained by elution of analytical samples on a Daicel ChiralPak AS-H column (250×4.6 mm, 5 μm) using the same eluent mixture with the flow rate indicated between brackets in the corresponding experimental protocol.

Semi-Preparative Chiral HPLC Method B:

The semi-preparative chiral HPLC is performed on a Daicel ChiralPak IA column (20×250 mm; 5 μm) using the eluent mixture, flow rate and detection conditions indicated between brackets in the corresponding experimental protocol. The retention times are obtained by elution of analytical samples on a Daicel ChiralPak IA column (4.6×250 mm; 5 μm) using the same eluent mixture with the flow rate indicated between brackets in the corresponding experimental protocol.

Semi-Preparative Chiral HPLC Method C:

The semi-preparative chiral HPLC is performed on a Daicel ChiralPak AD-H column (30×250 mm, 5 μm) using the eluent mixture, flow rate and detection conditions indicated between brackets in the corresponding experimental protocol. The retention times are obtained by elution of analytical samples on a Daicel ChiralPak AD-H column (4.6×250 mm, 5 μm) using the same eluent mixture with the flow rate indicated between brackets in the corresponding experimental protocol.

Semi-Preparative Chiral HPLC Method D:

The semi-preparative chiral HPLC is performed on a Daicel ChiralPak AY-H column (20×250 mm, 5 μm) using the eluent mixture, flow rate and detection conditions indicated between brackets in the corresponding experimental protocol. The retention times are obtained by elution of analytical samples on a Daicel ChiralPak AY-H column (4.6×250 mm, 5 μm) using the same eluent mixture with the flow rate indicated between brackets in the corresponding experimental protocol.

Procedures:

Procedure A:

To a solution of the THP-protected hydroxamic acid derivative (0.15 mmol) in MeOH (1.2 mL) and water (0.4 mL) is added 2M HCl (0.6 mL; 1.2 mmol). The reaction mixture is stirred at rt until completion. The reaction mixture, after neutralization with sat. aq. NaHCO$_3$, is extracted with DCM-MeOH (9-1, 3×20 mL). The evaporation residue is then purified by CC (DCM-MeOH) or by prep-HPLC using a suitable method.

Procedure B:

To the THP-protected hydroxamic acid derivative (0.368 mmol) in EtOH (2 mL) is added PPTS (0.139 g; 0.55 mmol). The mixture is stirred at about 80° C. for 5 h. After cooling to rt, the solvent is removed in vacuo. The residue is dissolved in DCM-MeOH (9-1, 10 mL) and washed with sat. aq. NaHCO$_3$ (5 mL). The org. layer is dried over MgSO$_4$, filtered and concentrated to dryness. The residue is purified by CC (DCM-MeOH) or by prep-HPLC using a suitable method.

Procedure C:

A solution of the THP-protected hydroxamic acid derivative (0.070 g, 0.119 mmol) in 4M HCl in dioxane (1 mL) was stirred 10 min at rt. The mixture was directly purified by prep-HPLC using a suitable method.

Procedure D:

CuCl (0.486 g, 4.91 mmol) and NH$_2$OH.HCl (3.4 g, 48.9 mmol) are dissolved in nBuNH$_2$ (12.1 mL) and water (20 mL). The terminal alkyne (22.1 mmol) and nBuNH$_2$ (12.1 mL) are added. The reaction mixture is ice-chilled and the halo-alkyne (29.1 mmol) in dioxane (6.5 mL) is added at 0° C. The reaction proceeds 1 h at that temperature. The reaction mixture is then allowed to warm up to rt over 1 h. Water (200 mL) and EA (250 mL) are added and two phases are separated. The aq. layer is extracted with EA (200 mL). The evaporation residue is then purified by CC or by prep-HPLC using a suitable method to afford the bis-alkyne product.

PREPARATIONS

Preparation A: (RS)-tert-butyl 4-amino-2-methyl-2-(methylsulfonyl)butanoate

A.i. (RS)-tert-butyl 2-(methylsulfonyl)propanoate

To a suspension of sodium methanesulfinate (100 g; 929 mmol) in tBuOH (350 mL) was added tert-butyl 2-bromopropionate (150 mL; 877 mmol). The reaction mixture was stirred at about 90° C. for 24 h under nitrogen atmosphere, then cooled to rt and concentrated to dryness. The residue was partitioned between water (750 mL) and EA (600 mL). The aq. layer was extracted with EA (2×500 mL). The evaporation residue afforded the title compound as a yellowish solid (175 g, 96% yield).

$^1$H NMR (d6-DMSO) δ: 4.24 (q, J=7.2 Hz, 1H); 3.11 (s, 3H); 1.45 (s, 9H); 1.40 (d, J=7.2 Hz, 3H).

A.ii. (RS)-tert-butyl 4-bromo-2-methyl-2-(methylsulfonyl)butanoate

To an ice-chilled suspension of intermediate A.i (130 g; 626 mmol) in DMF (750 mL) was added portionwise NaH (60% in mineral oil; 32.1 g; 802 mmol) for 1.5 h, keeping IT below 7° C. The mixture was stirred at 0° C. for 1.5 h, allowed to reach rt and stirred at rt for 0.5 h. The mixture was cooled down to 12° C. with an ice bath and 1,2-dibromoethane (166 mL; 1.9 mol) was then added dropwise, keeping IT below 22° C. The reaction mixture was stirred at rt for 2 h. The mixture was poured into cold water (1 L) and Et$_2$O (1 L) and the aq. layer was extracted with Et$_2$O (2×750 mL). The org. layer was washed with cold water (2×500 mL). The evaporation residue was purified by CC (Hept-EA) to afford the title compound as a pale yellowish oil (116.8 g; 59% yield).

$^1$H NMR (d$_6$-DMSO) δ: 3.71-3.63 (m, 1H); 3.45-3.37 (m, 1H); 3.12 (s, 3H); 2.72-2.62 (m, 1H); 2.43-2.33 (m, 1H); 1.49 (s, 3H); 1.46 (s, 9H).

A.iii. (RS)-tert-butyl 4-azido-2-methyl-2-(methylsulfonyl)butanoate

To a solution of intermediate A.ii (70.3 g; 223 mmol) in DMF (400 mL) was added NaN$_3$ (54.6 g; 831 mmol). The reaction mixture was stirred at 80° C. overnight, before being cooled to rt. Water (500 mL) and EA (500 mL) were added. The aq. layer was extracted with EA (2×500 mL) and the org. layer was washed with water (2×500 mL). The evaporation residue was triturated in Hept, filtered and washed with Hept to afford the title compound as a white solid (59.6 g; 96% yield).

$^1$H NMR (d6-DMSO) δ: 3.66-3.60 (m, 1H); 3.35-3.29 (overlapped m, 1H); 3.11 (s, 3H); 2.49-2.43 (m, 1H); 2.04-1.96 (m, 1H); 1.46 (s, 9H); 1.44 (s, 3H).

MS (ESI, m/z): 278.95 [M+H$^+$] for $C_{10}H_{19}N_3O_4S$; $t_R$=0.80 min.

A.iv. (RS)-tert-butyl 4-amino-2-methyl-2-(methylsulfonyl)butanoate

A solution of intermediate A.iii (45 g; 162 mmol) in a mixture of tBuOH-EA (1-1, 900 mL) was treated with 10% Pd/C (2.3 g). The suspension was stirred at rt under hydrogen for 4 h. Then 10% Pd/C (0.5 g) was added to the suspension and the reaction was stirred under hydrogen for 2 days. The catalyst was filtered off and the filtrate concentrated to dryness to afford the crude material which crystallized on standing (grey solid; 40.6 g; 99% yield).

$^1$H NMR (d6-DMSO) δ: 3.06 (s, 3H); 2.75-2.63 (m, 1H); 2.53-2.40 (overlapped m, 1H); 2.28-2.16 (m, 1H); 1.85-1.74 (m, 1H); 1.44 (s, 9H); 1.40 (s, 3H).

MS (ESI, m/z): 252.03 [M+H$^+$] for $C_{10}H_{21}NO_4S$; $t_R$=0.45 min.

Preparation B: (R)-tert-butyl 4-amino-2-methyl-2-(methylsulfonyl)butanoate

B.i. (R)-tert-butyl 4-azido-2-methyl-2-(methylsulfonyl)butanoate

Intermediate A.iii (184 g) was separated by semi-preparative chiral HPLC Method A (Hept-iPrOH 4-1; flow rate: 570 mL/min; UV detection at 235 nm); the respective retention times were 8.3 and 10.7 min. The title (R)-enantiomer, identified as the second eluting compound, was obtained as a light orange oil (90.7 g).

$^1$H NMR (d$_6$-DMSO) δ: 3.66-3.60 (m, 1H); 3.35-3.29 (overlapped m, 1H); 3.11 (s, 3H); 2.50-2.43 (overlapped m, 1H); 2.04-1.97 (m, 1H); 1.46 (s, 9H); 1.44 (s, 3H).

B.ii. (R)-tert-butyl 4-amino-2-methyl-2-(methylsulfonyl)butanoate

Starting from intermediate B.i (45 g; 162 mmol) and proceeding in analogy to Preparation A, step A.iv, the title compound was obtained as a grey solid (40.6 g; 99% yield).

$^1$H NMR (d$_6$-DMSO) δ: 3.06 (s, 3H); 2.75-2.63 (m, 11H); 2.53-2.40 (overlapped m, 1H); 2.28-2.16 (m, 1H); 1.85-1.74 (m, 1H); 1.44 (s, 9H); 1.40 (s, 3H).

MS (ESI, m/z): 252.03 [M+H$^+$] for $C_{10}H_{21}NO_4S$; $t_R$=0.45 min.

Preparation C: tert-butyl (R)-4-(6-iodo-3-oxo-1H-pyrrolo[1,2-c]imidazol-2(3H)-yl)-2-methyl-2-(methylsulfonyl)butanoate

FIRST METHOD

C.i. (RS)-tert-butyl 4-(((4-iodo-1H-pyrrol-2-yl)methyl)amino)-2-methyl-2-(methylsulfonyl)butanoate To a solution of the compound of Preparation A (24.631 g; 98 mmol) in dry THF (470 mL) was added 4-iodo-1H-pyrrole-2-carbaldhehyde (20.625 g; 93.3 mmol, commercial). The reaction mixture was stirred 2 h. MeOH (144 mL) was added and the resulting mixture was cooled to −20° C. NaBH$_4$ (3.578 g, 94.6 mmol) was added portionwise. Once the addition completed, the reaction proceeded at 0° C. for 1 h. Ice-water (330 mL) was added portionwise, keeping IT below 10° C. DCM (600 mL) was added. The two layers were separated and the aq. layer was extracted twice with DCM (2×250 mL). The combined org. layers were washed with sat. aq. NaHCO$_3$ (300 mL). The evaporation residue was further co-evaporated twice with toluene (2×150 mL) to afford, after drying under high vacuum, of the crude title product as a brown oil (43.87 g; >95% yield).

$^1$H NMR (d$_6$-DMSO) δ: 10.88 (br. s, 1H); 6.77 (s, 1H); 5.97 (s, 1H); 3.63-3.49 (m, 2H); 3.06 (s, 3H); 2.60-2.55 (overlapped m, 1H); 2.42-2.34 (m, 1H); 2.32-2.24 (m, 1H); 2.05-1.95 (overlapped, m, 1H); 1.84-1.76 (m, 1H); 1.40 (s, 9H); 1.38 (s, 3H).

MS (ESI, m/z): 456.67 [M+H$^+$] for $C_{15}H_{25}N_2O_4IS$; $t_R$=0.63 min.

C.ii. (RS)-tert-butyl 4-(6-bromo-3-oxo-1H-pyrrolo[1,2-c]imidazol-2(3H)-yl)-2-methyl-2-(methylsulfonyl)butanoate To a solution of intermediate C.i (60.88 g; 124 mmol) in dry THF (329 mL) was added, at 0° C., CDI (21.12 g; 130 mmol). The reaction mixture was then stirred at rt for 3 h. After cooling to 0° C., NaH (60% dispersion in oil, 0.758 g; 17.4 mmol) was added portionwise. After 2 h stirring, a second portion of NaH (60% dispersion in oil, 0.758 g; 17.4 mmol) was added. The reaction proceeded 2 h and sat. aq. NH$_4$Cl (300 mL) was carefully added. The mixture was further diluted with water (200 mL) and EA (1 L). The two phases were separated and the aq. phase was extracted twice with EA (2×500 mL). The evaporation residue was purified by CC (DCM-EA) to afford the title compound as a white solid (40.2 g, 67% yield).

$^1$H NMR (CDCl$_3$) δ: 7.20 (d, J=0.9 Hz, 1H); 6.16 (q, J=1.4 Hz, 1H); 4.43 (m, 1H); 4.29 (m, 1H); 3.80 (m, 1H); 3.57 (m, 1H); 3.05 (s, 3H); 2.58 (m, 1H); 2.18 (m, 1H); 1.71 (s, 3H); 1.43 (s, 9H).

MS (ESI, m/z): 482.85 [M+H$^+$] for $C_{16}H_{23}N_2O_5IS$; $t_R$=0.89 min.

C.iii. Tert-butyl (R)-4-(6-iodo-3-oxo-1H-pyrrolo[1,2-c]imidazol-2(3H)-yl)-2-methyl-2-(methylsulfonyl)butanoate Intermediate C.ii (22.8 g) was separated by semi-preparative chiral HPLC Method B (MeOH-EtOH 1-1; flow rate: 100 mL/min; UV detection at 243 nM); the respective retention times were 6.2 and 6.8 min. The title (R)-enantiomer, identified as the second eluting compound, was obtained as a white solid (9.5 g).

$^1$H NMR (CDCl$_3$) δ: 7.20 (d, J=0.9 Hz, 1H); 6.16 (q, J=1.4 Hz, 1H); 4.43 (m, 1H); 4.29 (m, 1H); 3.80 (m, 1H); 3.57 (m, 1H); 3.05 (s, 3H); 2.58 (m, 1H); 2.18 (m, 1H); 1.71 (s, 3H); 1.43 (s, 9H).

MS (ESI, m/z): 482.85 [M+H$^+$] for $C_{16}H_{23}N_2O_5IS$; $t_R$=0.89 min.

SECOND METHOD

Alternatively, starting from the compound of Preparation B (3.8 g; 15 mmol) and 4-iodo-1H-pyrrole-2-carbaldehyde (3.5 g; 15.8 mmol) and proceeding as described in steps C.i (55% yield) and C.ii (75% yield), the title compound was obtained as a white solid (3.15 g).

The product obtained by the SECOND METHOD had NMR data equivalent to those reported for the compound obtained by the FIRST METHOD.

Preparation D: (2R)-4-(6-ethynyl-3-oxo-1H-pyrrolo[1,2-c]imidazol-2(3H)-yl)-2-methyl-2-(methylsulfonyl)-N-((tetrahydro-2H-pyran-2-yl)oxy)butanamide D.i. (R)-4-(6-iodo-3-oxo-1H-pyrrolo[1,2-c]imidazol-2(3H)-yl)-2-methyl-2-(methylsulfonyl)butanoic acid To an ice-chilled solution of the compound of Preparation C (40 g; 85.2 mmol) in DCM (238 mL) was added $Et_3SiH$ (14.6 mL; 91.4 mmol) and TFA (182 mL, 2.3 mol) over 15 min. The resulting solution was stirred at rt for 5 h. The reaction mixture was cooled to 0° C. and dry $Et_2O$ (450 mL) was added dropwise over 1 h. The resulting suspension was stirred 1 h, filtered and washed with $Et_2O$ (3×100 mL). The solid was dried to afford the title compound as an off-white solid (33.56 g; 95% yield).

$^1$H NMR (d6-DMSO) δ: 13.81 (m, 1H); 7.32 (d, J=0.9 Hz, 1H); 6.23 (m, 1H); 4.47-4.35 (m, 2H); 3.59 (m, 1H); 3.53-3.40 (overlapped m, 1H); 3.12 (s, 3H); 2.59-2.48 (overlapped m, 1H); 2.04 (m, 1H); 1.53 (s, 3H).

MS (ESI, m/z): 426.9 [M+H$^+$] for $C_{12}H_{15}N_2O_5IS$; $t_R$=0.69 min.

D. ii. (2R)-4-(6-iodo-3-oxo-1H-pyrrolo[1,2-c]imidazol-2(3H)-yl)-2-methyl-2-(methylsulfonyl)-N-((tetrahydro-2H-pyran-2-yl)oxy)butanamide To a suspension of intermediate D.i (33.56 g; 78.7 mmol) in THF (380 mL) were added DIPEA (74 mL; 433 mmol) and THPO—$NH_2$ (14.56 g; 118 mmol). The mixture was cooled down to 0° C. and T3P (50% in EA, 72 mL; 181 mmol) was added over 30 min. After 1 h at 0° C., DIPEA (12 mL; 70 mmol) and T3P (50% in EA, 30 mL, 75 mmol) were added. The reaction proceeded further 1 h and sat. aq. $NaHCO_3$ (200 mL) was added at 0° C. The mixture was diluted with water (100 mL) and EA (200 mL). The two layers were separated and the aq. layer was extracted with EA (200 mL). The evaporation residue was purified by CC (Hept-EA gradient) to afford the title compound as a white solid (32.46 g; 78% yield).

$^1$H NMR (d6-DMSO) δ (mixture of steroisomers): 11.37 (m, 0.5H); 11.34 (m, 0.5H); 7.32 (d, J=7.9 Hz, 1H); 6.21 (dd, J=1.3, 3.0 Hz, 1H); 4.86 (s, 0.5H); 4.48-4.38 (m, 2.5H); 4.05-4.00 (m, 0.5H); 3.98-3.92 (m, 0.5H); 3.55-3.42 (overlapped m, 3H); 3.07 (s, 1.5H); 3.04 (s, 1.5H); 2.70-2.55 (overlapped m, 1H); 2.01-1.92 (m, 1H); 1.70-1.61 (m, 2H); 1.57-1.45 (m, 7H).

MS (ESI, m/z): 525.9 [M+H$^+$] for $C_{17}H_{24}N_3O_6IS$; $t_R$=0.78 min.

D.iii. (R)-2-methyl-2-(methylsulfonyl)-4-(3-oxo-6-((trimethylsilyl)ethynyl)-1H-pyrrolo[1,2-c]imidazol-2(3H)-yl)-N—(((RS)-tetrahydro-2H-pyran-2-yl)oxy)butanamide CuI (1.4 g; 7.29 mmol) and $PdCl_2(PPh_3)_2$ (2.36 g; 3.5 mmol) were introduced in a two-necked round-bottom flask. After flushing with nitrogen for 30 min, a solution of intermediate D.ii (19.16 g; 36.5 mmol) in degassed THF (270 mL) was added, followed by trimethylsilylacetylene (7.8 mL, 54.7 mmol). Degassed TEA (15.3 mL, 109 mmol) was added and the reaction proceeded at 50° C. for 2 h. The mixture was concentrated to dryness and the residue was purified by CC (Hept-EA) to afford the title compound as a yellow foam (16.25 g, 90% yield).

$^1$H NMR (d$_6$-DMSO) δ (mixture of stereoisomers): 11.40-11.25 (m, 1H); 7.39-7.29 (m, 1H); 6.21-6.12 (m, 1H); 4.91-4.80 (m, 0.5H); 4.53-4.45 (m, 0.5H); 4.44-4.32 (m, 2H); 4.05-3.96 (m, 1H); 3.51-3.34 (m, 3H); 3.06 (s, 1.5H); 3.03 (s, 1.5H); 2.72-2.53 (m, 1H); 2.04-1.88 (m, 1H); 1.68-1.60 (overlapped m, 2H); 1.56 (s, 1.5H); 1.54 (s, 1.5H); 1.54-1.44 (overlapped m, 4H); 0.17 (s, 9H).

MS (ESI, m/z): 496.01 [M+H$^+$] for $C_{22}H_{33}N_3O_6SSi$; $t_R$=0.90 min.

D. iv. (RS)-4-(6-ethynyl-3-oxo-1H-pyrrolo[1,2-c]imidazol-2(3H)-yl)-2-methyl-2-(methylsulfonyl)-N—(((RS)-tetrahydro-2H-pyran-2-yl)oxy)butanamide To a solution of intermediate D.iii (14.1 g; 28.5 mmol) in THF (62 mL) was added TBAF (1M in THF, 29.2 mL; 29.2 mmol). The mixture was stirred for 20 min. Cold water was added (100 mL) and the mixture was concentrated to a minimal volume. EA was added (100 mL) and the 2 phases were separated. The water phase was extracted with EA (3×100 mL). The evaporation residue was purified by CC (DCM-MeOH) to afford the title compound as a yellow foam (11.74 g; 97% yield).

$^1$H NMR (d$_6$-DMSO) δ (mixture of stereoisomers): 11.36-11.32 (br. s, 0.5H); 11.32-11.28 (br. s, 0.5H); 7.40-7.35 (m, 1H); 6.20-6.16 (m, 1H); 4.88-4.83 (m, 0.5H); 4.52-4.46 (m, 0.5H) 4.44-4.38 (m, 2H); 4.08-3.89 (overlapped m, 1H); 3.94 (s, 1H); 3.54-3.38 (m, 3H); 3.05 (s, 1.5H); 3.03 (s, 1.5H); 2.50-2.40 (overlapped m, 1H); 2.04-1.86 (m, 1H); 1.69-1.61 (m, 2H); 1.56 (s, 1.5H); 1.54 (s, 1.5H); 1.52-1.42 (overlapped m, 4H).

MS (ESI, m/z): 423.98 [M+H$^+$] for $C_{19}H_{25}N_3O_6S$; $t_R$=0.74 min.

Preparation E: 3-(2-((di-tert-butoxyphosphoryl)oxy)phenyl)propanoic acid

E.i. Methyl 3-(2-((di-tert-butoxyphosphoryl)oxy)phenyl)propanoate

To a solution of methyl 3-(2-hydroxyphenyl)propionate (5 g; 30 mmol) in THF (102 mL), cooled at 0° C., was added tetrazole (0.45M in MeCN, 92 mL; 0.042 mol) and di-tert-butyl diisopropylphosphoramidite (12 mL; 36 mmol). The reaction mixture was heated at 40° C. for 24 h. After cooling to 0° C., $H_2O_2$ (30% aq.; 22 mL) was added dropwise at 0° C., keeping IT below 10° C. The solution was stirred for 1.5 h at 0° C. Water (200 mL) was added. The aq. layer was extracted with EA (3×100 mL) and the org. layers were washed with 10% aq. $NaHSO_3$ (100 mL). The evaporation residue was purified by CC (Hept-EA) to afford the title compound as a colourless oil (6.2 g; 60% yield).

$^1$H NMR (d6-DMSO) δ: 7.35-7.20 (m, 3H); 7.11 (m, 1H); 3.60 (s, 3H); 2.94-2.85 (m, 2H); 2.66-2.56 (m, 2H); 1.45 (s, 18H).

MS (ESI, m/z): 373.0 [M+H$^+$] for $C_{18}H_{29}O_6P$; $t_R$=0.91 min.

E.ii. 3-(2-((di-tert-butoxyphosphoryl)oxy)phenyl)propanoic acid

To a solution of intermediate E.i (4.3 g; 0.011 mol) in THF-MeOH-water (2-2-1; 100 mL) was added LiOH.$H_2O$ (1.94 g; 46 mmol). The reaction mixture was stirred at rt for 1.5 h. The volatiles were removed in vacuo and the residue was diluted with water (20 mL) and washed with TBME (2×100 mL). This org. layer was discarded. The aq. layer was acidified with 10% aq. citric acid (100 mL) and extracted with EA (3×100 mL). The evaporation residue afforded the title compound as a white solid (3.2 g, 79% yield).

$^1$H NMR (d6-DMSO) δ: 12.14 (s, 1H); 7.30-7.26 (m, 2H); 7.24 (m, 1H); 7.11 (t, J=7.2 Hz, 1H); 2.88-2.82 (m, 2H); 2.55-2.51 (overlapped m, 2H); 1.45 (s, 18H).

MS (ESI, m/z): 359.0 [M+H$^+$] for $C_{17}H_{27}O_6P$; $t_R$=0.81 min.

Preparation F:
((1S,2S)-2-(bromoethynyl)cyclopropyl)methyl di-tert-butyl phosphate F.i. ((1S,2S)-2-(bromoethynyl)cyclopropyl)methanol To a solution of ((1S,2S)-2-(bromoethynyl)cyclopropyl) methyl acetate (prepared as described in WO 2005/036964; 1 g; 4.61 mmol) in MeOH (22.9 mL) was added $K_2CO_3$ (1.273 g, 9.21 mmol). The suspension was stirred 30 min. The solvent was evaporated under reduced pressure and the residue was diluted in DCM-MeOH (9-1, 100 mL). The org. layer was washed with 15% aq. $NaHSO_4$ (30 mL), dried over $MgSO_4$, filtered and concentrated to dryness to afford the title product as a colourless oil (0.803 g; quant.).

$^1$H NMR (d6-DMSO) δ: 4.63 (t, J=5.7 Hz, 1H); 3.37 (m, 1H); 3.19 (m, 1H); 1.29-1.20 (m, 2H); 0.76 (m, 1H); 0.70 (ddd, J=4.2, 6.0, 8.5 Hz, 1H).

F.ii. ((1S,2S)-2-(bromoethynyl)cyclopropyl)methyl di-tert-butyl phosphate

To a solution of intermediate F.i (0.570 g; 3.26 mmol) in THF (5 mL) cooled to 0° C. was added portionwise NaH (60% in mineral oil; 0.195 g; 4.89 mmol). The mixture was stirred at 0° C. for 5 min and at rt for 1 h. After cooling to 0° C., di-tert-butyl phosphorochloridate (prepared as described in WO 2010/032147, 1.043 g; 4.56 mmol) was added dropwise. The mixture was stirred for 5 h. EA (50 mL) and water (50 mL) were added. The two layers were separated and the aq. layer was extracted with EA (50 mL). The evaporation residue was purified by CC (Hept-EA) to afford the title compound as a light yellow oil (0.638 g; 53% yield).

$^1$H NMR (d6-DMSO) δ: 8.47 (br. s, 2H); 3.57 (s, 1H); 3.11-3.19 (m, 2H); 3.09-3.00 (m, 2H); 1.96-1.89 (m, 2H); 1.89-1.80 (n, 2H).

MS (ESI, m/z): 366.91 [M+H$^+$] for $C_{14}H_{24}O_4BrP$; $t_R$=0.92 min.

Preparation G: ((1R,2R)-2-(bromoethynyl)-1-fluorocyclopropyl)methyl di-tert-butyl phosphate G.i. ((1R*,2R*)-2-(((tert-butyldiphenylsilyl)oxy) methyl)-1 fluorocyclopropyl)methanol To a solution of ethyl (1R*,2R*)-2-(((tert-butyldiphenyl-silyl)oxy)methyl)-1-fluorocyclopropane-1-carboxylate (0.5 g; 1.25 mmol; prepared as described in Sakagami et al., Bioorg. Med. Chem. (2008), 16(8), 4359-4366) in THF (9 mL), cooled to −78° C., was added dropwise LiBH$_4$ (2M in THF; 2.2 mL; 4.4 mmol). The reaction mixture was allowed to reach rt and stirred at rt for 24 h. MeOH (2 mL) was carefully added, the reaction mixture was stirred for 20 min, concentrated to dryness and partitioned between water (10 mL) and DCM (15 mL). The aq. layer was extracted with DCM (2×10 mL). The evaporation residue afforded the title compound as a colourless oil (0.429 g; 96% yield).

$^1$H NMR (CDCl$_3$) δ: 7.72-7.66 (m, 4H); 7.45-7.36 (m, 6H); 3.89 (ddd, J=1.6, 6.0, 11.0 Hz, 1H); 3.83-3.80 (m, 1H); 3.78-3.70 (m, 2H); 1.74 (t, J=6.4 Hz, 1H); 1.33-1.24 (m, 1H); 1.05 (s, 9H); 0.88-0.79 (m, 2H).

MS (ESI, m/z): 358.95 [M+H$^+$] for $C_{21}H_{27}O_2FSi$; $t_R$=1.01 min.

G.ii. ((1R*,2R*)-2-(((tert-butyldiphenylsilyl)oxy) methyl)-1-fluorocyclopropyl)methyl benzoate To a solution of intermediate G.i (5.51 g, 15.4 mmol) in THF (93 mL) was added TEA (6 mL; 43.1 mmol). BzCl (3.6 mL; 30.7 mmol) was added dropwise over 2 min at 0° C. The reaction mixture was stirred at 0° C. for 5 h before being poured onto water (75 mL). The aq. layer was extracted with EA (3×50 mL). The combined org. layers were dried over MgSO$_4$ and concentrated to dryness. The residue was purified by CC (Hept-EA) to afford the title compound as a colourless oil (6.49 g; 91% yield).

$^1$H NMR (CDCl$_3$) δ: 8.12-8.09 (m, 2H); 7.70-7.67 (m, 4H); 7.56 (m, 1H); 7.44-7.40 (m, 4H); 7.38-7.35 (m, 4H); 4.62 (m, 1H); 4.51 (ddd, J=1.1, 13.0, 23.8 Hz, 1H); 3.93 (ddd, J=1.5, 5.6, 11.0 Hz, 1H); 3.70 (ddd, J=1.1, 8.4, 10.9 Hz, 1H); 1.46 (m, 1H); 1.30 (m, 1H); 1.02 (s, 7H); 0.97 (m, 1H); 0.91-0.84 (m, 2H).

MS (ESI, m/z): 463.07 [M+H$^+$] for $C_{28}H_{31}O_3FSi$; $t_R$=1.14 min.

G.iii. ((1R*,2R*)-1-fluoro-2-(hydroxymethyl)cyclo-propyl)methyl benzoate

Starting from intermediate G.ii (6.49 g; 14 mmol) and proceeding successively in analogy to Preparation D, step D.iv (89% yield), the title compound (2.81 g) was obtained, after purification by CC (DCM-MeOH), as a yellowish oil.

$^1$H NMR (CDCl$_3$) δ: 8.10-8.08 (m, 2H); 7.58 (m, 1H); 7.48-7.45 (m, 2H); 4.64 (m, 1H); 4.55 (m, 1H); 3.97 (ddd, J=1.5, 5.8, 11.8 Hz, 1H); 3.68 (ddd, J=1.4, 8.7, 11.8 Hz, 1H); 1.52 (m, 1H); 1.12-1.04 (m, 2H).

G.iv. ((1R*,2R*)-1-fluoro-2-formylcyclopropyl)methyl benzoate

To a solution of intermediate G.iii (2.77 g, 12.4 mmol) in DCM (39 mL), cooled at −10° C., was added DIPEA (8.5 mL; 49.7 mmol). A solution of Pyr.SO$_3$ complex (4.65 g, 13.2 mmol) in DMSO (20 mL) was then added dropwise over 1 h, keeping IT below −6° C. The reaction mixture was stirred for 2 h at −10° C. The reaction mixture was partitioned between water (50 mL) and DCM (30 mL). The two layers were decanted and the aq. layer was extracted with DCM (50 mL). The evaporation residue was purified by CC (Hept-EA gradient) to afford the title product as a yellow oil (2.31 g; 84% yield).

MS (ESI, m/z): 223.10 [M+H$^+$] for $C_{12}H_{11}O_3F$; $t_R$=0.79 min.

G.v. ((1R,2R)-2-(2,2-dibromovinyl)-1-fluorocyclo-propyl)methyl benzoate

To a solution of CBr$_4$ (6.25 g, 18.5 mmol) in DCM (13 mL) cooled at −20° C., was added dropwise over 30 min a solution of PPh₃ (10.04 g, 36.8 mmol) in DCM (22.4 mL). The mixture was kept stirring at this temperature for 30 min and then cooled to −78° C. TEA (2.5 mL, 17.9 mmol) was added followed by a solution of intermediate G.iv (2.07 g, 9.31 mmol) in DCM (18 mL), keeping the IT below −75° C. The mixture was stirred at this temperature for 2 h. The reaction mixture was warmed to 15° C. over 20 min. The reaction mixture was diluted in Et₂O (100 mL), filtered and washed with Et₂O (20 mL). The filtrate was concentrated to dryness and the residue was purified by CC (Hept-EA) to afford the title compound (2.71 g, 77% yield) as a colorless oil. After separation by semi-preparative chiral HPLC Method D (Hept-EtOH 3-7; flow rate: 16 mL/min, UV detection at 224 nm), the title enantiomer (first-eluting enantiomer) was obtained as a white solid (1.25 g). The retention time on analytical chiral HPLC (Hept-EtOH 3-7; flow rate: 0.8 mL/min) was 5.3 min.

$^1$H NMR (d6-DMSO) δ: 8.01-7.99 (m, 2H); 7.69 (m, 1H); 7.58-7.54 (m, 2H); 6.38 (dd, J=1.4, 8.9 Hz, 1H); 4.75-4.57 (m, 2H); 2.09 (m, 1H); 1.55-1.48 (m, 2H).

G.vi. ((1R,2R)-2-(bromoethynyl)-1-fluorocyclopropyl)methanol

To a solution of intermediate G.v (2.05 g, 5.42 mmol) in THF (20 mL) was added TBAF (1M in THF, 22 mL; 21.7 mmol). The mixture was stirred overnight. The reaction mixture was diluted with EA (50 mL) and water (30 mL). The two layers were separated and the org. layer was extracted with EA (3×50 mL). The evaporation residue was purified by CC (Hept-EA) to afford the title compound as a yellowish oil (0.2 g; 19% yield).

$^1$H NMR (d6-DMSO) δ: 5.22-5.14 (m, 1H); 3.70-3.54 (m, 2H); 1.73 (m, 1H); 1.27-1.17 (m, 2H).

G.vii. ((1R,2R)-2-(bromoethynyl)-1-fluorocyclopropyl)methyl di-tert-butyl phosphate Starting from intermediate G.vi (0.258 g; 1.34 mmol) and proceeding in analogy to Preparation F, step F.ii., the title compound was obtained as a yellowish oil (0.386 g; 75% yield).

$^1$H NMR (d6-DMSO) δ: 4.18-3.99 (m, 2H); 1.92 (m, 1H); 1.41 (s, 18H); 1.39-1.30 (m, 2H).

MS (ESI, m/z): 385.0 [M+H$^+$] for C₁₄H₂₄O₄BrFP; $t_R$=0.91 min.

REFERENCE EXAMPLES

Reference Example 1: (R)—N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide RE1.i. (2R)-4-(6-((1-(((tert-butyldiphenylsilyl)oxy)methyl)cyclopropyl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide Starting from the compound of Preparation D (9.37 g; 22.1 mmol) and ((1-(bromoethynyl)cyclopropyl)methoxy)(tert-butyl)diphenylsilane (prepared as described in WO 2015/036964, 12.02 g; 29.1 mmol) and proceeding in analogy to Procedure D (75% yield), the title compound was obtained, after purification by CC (Hept-EA-MeOH), as a yellowish foam (12.49 g).

MS (ESI, m/z): 756.16 [M+H$^+$] for C₄₁H₄₉N₃O₇SSi; $t_R$=1.11 min.

RE1.ii. (2R)-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)-N-((tetrahydro-2H-pyran-2-yl)oxy)butanamide To a solution of intermediate RE1.i (21.190 g, 28 mmol) in THF (675 mL) was added TBAF (1M in THF, 56 mL; 56 mmol). It was stirred for 9 h. Water (200 mL) was added and the solvent was removed in vacuo. The residue was taken up in EA (200 mL). The two layers were separated and the aq. layer was extracted twice with EA (2×200 mL). The evaporation residue was purified by CC (Hept-EA-MeOH) to afford the title compound as a pale yellow solid (13.76 g; 99% yield).

MS (ESI, m/z): 517.9 [M+H$^+$] for C₂₅H₃₁N₃O₇S; $t_R$=0.78 min.

RE1.iii. (R)—N-hydroxy-4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide Starting from intermediate RE1.ii (0.035 g; 0.066 mmol) and proceeding in analogy to Procedure B, the title compound was obtained, after precipitation in water, as a white solid (0.013 g; 46% yield).

$^1$H NMR (d₆-DMSO) δ: 10.97-10.87 (br. s, 1H); 9.20-9.14 (br. s, 1H); 7.53 (s, 1H); 6.24 (d, J=1.1 Hz, 1H); 5.00 (t, J=6.1 Hz, 1H); 4.43 (s, 2H); 3.51-3.45 (m, 1H); 3.38 (overlapped d, J=6.1 Hz, 2H); 3.41-3.36 (overlapped m, 1H); 3.06 (s, 3H); 2.63-2.54 (m, 1H); 2.00-1.92 (m, 1H); 1.52 (s, 3H); 0.91-0.88 (m, 2H); 0.87-0.83 (m, 2H).

MS (ESI, m/z): 433.98 [M+H$^+$] for C₂₀H₂₃N₃O₆S; $t_R$=0.66 min.

Reference Example 2: (R)—N-hydroxy-4-(6-(((1S,2S)-2-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamide RE2.i. ((1S,2S)-2-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl acetate Starting from the compound of Preparation D (0.4 g; 0.95 mmol) and ((1S,2S)-2-(bromoethynyl)cyclopropyl)methyl acetate (prepared as described in WO 2005/036964; 0.308 g; 1.42 mmol) and proceeding in analogy to Procedure D, the title compound was obtained, after purification by CC (DCM-MeOH) as a yellow foam (0.252 g; 56% yield).

$^1$H NMR (d₆-DMSO) δ: 10.98-10.89 (br. s, 1H); 9.21-9.14 (br. s, 1H); 7.53 (s, 1H); 6.24-6.23 (m, 1H); 4.42 (s, 2H); 3.99-3.93 (m, 1H); 3.85-3.78 (m, 1H); 3.52-3.44 (m, 1H); 3.42-3.34 (m, 1H); 3.05 (s, 3H); 2.62-2.54 (m, 1H); 2.03 (s, 3H); 2.00-1.91 (m, 1H); 1.63-1.57 (m, 1H); 1.57-1.53 (m, 1H); 1.52 (s, 3H); 1.04-0.99 (m, 1H); 0.97-0.91 (m, 1H).

MS (ESI, m/z): 475.99 [M+H$^+$] for C₂₂H₂₅N₃O₇S; $t_R$=0.76 min.

RE2.ii. (R)—N-hydroxy-4-(6-(5-((1S,2S)-2-(hydroxymethyl)cyclopropyl)penta-1,3-diyn-1-yl)-3-oxo-1H-pyrrolo[1,2-c]imidazol-2(3H)-yl)-2-methyl-2-(methylsulfonyl)butanamide Starting from intermediate RE2.i (0.252 g; 0.53 mmol) and proceeding in analogy to Preparation F, step F.i., the title compound was obtained, after purification by prep-HPLC (Method 2), as a white solid (0.085 g; 37% yield).
$^1$H NMR (d$_6$-DMSO) δ: 11.05-10.84 (br. s, 1H); 9.20-9.02 (br. s, 1H); 7.52 (s, 1H); 6.24 (d, J=1.1 Hz, 1H); 4.69 (t, J=5.8 Hz, 1H); 4.42 (s, 2H); 3.51-3.43 (m, 1H); 3.43-3.37 (m, 2H); 3.27-3.21 (m, 1H); 3.05 (s, 3H); 2.63-2.55 (m, 1H); 1.99-1.92 (m, 1H); 1.51 (s, 3H); 1.43-1.35 (m, 2H); 0.91-0.87 (overlapped m, 1H); 0.87-0.81 (overlapped m, 1H).

Reference Example 3: (R)-4-(6-(((1R,2R)-2-fluoro-2-(hydroxymethyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from the compound of Preparation D (0.7 g; 1.65 mmol) and intermediate G.vi (0.32 g; 1.66 mmol) and proceeding in analogy to Procedure D (92% yield) and Procedure B (76% yield), the title compound was obtained, after purification by CC (DCM-MeOH), as a yellow solid (0.52 g).
$^1$H NMR (d$_6$-DMSO) δ: 10.94 (s, 1H); 9.18 (s, 1H); 7.57 (d, J=0.7 Hz, 1H); 6.26 (d, J=1.2 Hz, 1H); 5.24 (t, J=6.1 Hz, 1H); 4.43 (s, 2H); 3.73-3.58 (m, 2H); 3.48 (m, 1H); 3.38 (m, 1H); 3.06 (s, 3H); 2.59 (m, 1H); 2.00-1.91 (m, 2H); 1.53 (s, 3H); 1.38-1.31 (m, 2H).
MS (ESI, m/z): 451.8 [M+H$^+$] for C$_{20}$H$_{22}$N$_3$O$_6$FS; t$_R$=0.65 min.

EXAMPLES OF COMPOUNDS ACCORDING TO THE INVENTION

Example 1: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 2-morpholinoacetate 1.i. (1-((2-((3R)-3-methyl-3-(methylsulfonyl)-4-oxo-4-((RS)-((tetrahydro-2H-pyran-2-yl)oxy)amino)butyl)-3-oxo-2,3-dihydro-1H-pyrrolo[1,2-c]imidazol-6-yl)buta-1,3-diyn-1-yl)cyclopropyl)methyl 2-morpholinoacetate To a solution of intermediate RE1.ii (0.228 g; 0.22 mmol) in DMF (1.73 mL) were added morpholin-4-yl-acetic acid (0.0384 g, 0.264 mmol), EDC (0.0844 g, 0.44 mmol), HOBT (0.0675 g, 0.44 mmol) and TEA (0.092 mL, 0.661 mmol). The reaction mixture was stirred overnight. The reaction mixture was diluted with DCM (30 mL). The resulting layer washed with sat. aq. NaHCO$_3$ (30 mL) and with sat. aq. NH$_4$Cl (30 mL), dried over MgSO$_4$, filtered and concentrated to dryness. The residue was purified by CC (DCM-MeOH) to afford the title product as a yellow gum (0.237 g; 84% yield).
$^1$H NMR (d6-DMSO) δ: 11.34 (br. s, 1H); 7.54 (s, 0.5H); 7.53 (s, 0.5H); 6.23 (m, 1H); 4.84 (m, 0.5H); 4.47 (m, 0.5H); 4.43-4.38 (m, 2H); 4.03 (s, 2H); 3.97 (m, 1H); 3.59-3.56 (m, 4H); 3.54-3.36 (m, 3H); 3.28 (s, 2H); 3.05 (s, 1.5H); 3.03 (s, 1.5H); 2.58 (m, 1H); 2.50 (overlapped m, 4H); 1.96 (m, 1H); 1.67-1.59 (m, 2H); 1.55 (s, 1.5H); 1.53 (s, 1.5H); 1.55-1.47 (m, 4H); 1.09-1.05 (m, 2H), 1.04-1.00 (m, 2H).

MS (ESI, m/z): 645.14 [M+H$^+$] for C$_{31}$H$_{40}$N$_4$O$_9$S; t$_R$=0.69 min.

1.ii. (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 2-morpholinoacetate Starting from intermediate 1.i (0.237 g; 0.368 mmol) and proceeding in analogy to Procedure B, the title compound was obtained, after purification by CC (DCM-MeOH), as a yellowish solid (0.091 g; 44% yield).
$^1$H NMR (d6-DMSO) δ: 10.94 (br. s, 1H); 9.18 (br. s, 1H); 7.54 (s, 1H); 6.23 (d, J=1.1 Hz; 1H); 4.42 (s, 2H); 4.03 (s, 2H); 3.59-3.56 (m, 4H); 3.48 (m, 1H); 3.38 (m, 1H); 3.32 (s, 2H); 3.05 (s, 3H); 2.59 (m, 1H); 2.50 (overlapped m, 4H); 1.96 (m, 1H); 1.52 (s, 3H); 1.07-1.05 (m, 2H); 1.04-1.01 (m, 2H).
MS (ESI, m/z): 505.96 [M+H$^+$] for C$_{26}$H$_{32}$N$_4$O$_8$S; t$_R$=0.60 min.

Example 2: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate Starting from intermediate RE1.ii (0.187 g; 0.36 mmol) and the compound of Preparation E (0.194 g; 0.54 mmol) and proceeding in analogy to the procedure of Example 1, step 1.i (34% yield) and Procedure C (71% yield), the title compound was obtained, after purification by prep-HPLC (Method 1), as a yellowish solid (0.056 g).
$^1$H NMR (d6-DMSO) δ: 10.95 (s, 1H); 9.17 (m, 1H); 7.55 (s, 1H); 7.29 (d, J=8.1 Hz, 1H); 7.25 (d, J=7.4 Hz, 1H); 7.17 (m, 1H); 7.03 (t, J=7.4 Hz, 1H); 6.25 (d, J=1.2 Hz, 1H); 4.42 (s, 2H); 4.00 (s, 2H); 3.50-3.40 (overlapped m, 2H); 3.06 (s, 3H); 2.90 (t, J=7.6 Hz, 2H); 2.68 (t, J=7.7 Hz, 2H); 2.60 (m, 1H); 1.96 (m, 1H); 1.52 (s, 3H); 1.08-1.05 (m, 2H); 1.02-1.00 (m, 2H).
MS (ESI, m/z): 662.0 [M+H$^+$] for C$_{29}$H$_{32}$N$_3$O$_{11}$PS; t$_R$=0.63 min.

Example 3: (R)-2-(3-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy)-3-oxopropyl)phenyl dihydrogen phosphate 3.i. (R)-4-(6-((1-(((tert-butyldiphenylsilyl)oxy)methyl)cyclopropyl)buta-1,3-diyn-1-yl)-3-oxo-1H-pyrrolo[1,2-c]imidazol-2(3H)-yl)-N-hydroxy-2-methyl-2-(methylsulfonyl)butanamide Starting from intermediate RE1.i (0.353 g; 0.467 mmol) and proceeding in analogy to Procedure B, the title compound was obtained as a yellowish foam (0.316 g; >95% yield).
$^1$H NMR (d6-DMSO) δ: 10.95 (br. s, 1H); 9.18 (br. s, 1H); 7.63-7.68 (m, 4H); 7.56 (d, J=1 Hz, 1H); 7.42-7.51 (m, 6H); 6.26 (d, J=1 Hz, 1H); 4.44 (s, 2H); 3.62 (s, 2H), 3.48 (m, 1H); 3.39 (m, 1H); 3.07 (s, 3H); 2.60-2.64 (m, 1H); 1.97 (m, 1H); 1.50 (s, 3H); 1.03 (s, 9H); 0.99-0.96 (m, 2H); 0.88-0.84 (m, 2H).
MS (ESI, m/z): 672.14 [M+H$^+$] for C$_{36}$H$_{41}$N$_3$O$_6$SSi; t$_R$=1.03 min.

3.ii. (R)-2-(3-((4-(6-((1-(hydroxymethyl)cyclopropyl)buta-1,3-diyn-1-yl)-3-oxo-1H-pyrrolo[1,2-c]imidazol-2(3H)-yl)-3-methyl-2-(methylsulfonyl)butanamido)oxy)-3-oxopropyl)phenyl dihydrogen phosphate Starting from intermediate 3.i (0.31 g; 0.47 mmol) and the compound of Preparation E (0.202 g; 0.56 mmol), and proceeding in analogy to the procedures of Example 1, step 1.i (74% yield), Reference Example 1, step RE1.ii (67% yield) and Procedure C (51% yield), the title compound was obtained, after purification by prep-HPLC (Method 2), as a white solid (0.059 g).

$^1$H NMR (d6-DMSO) δ: 7.55 (d, J=0.7 Hz, 1H); 7.31 (d, J=8.0 Hz, 1H); 7.27 (d, J=7.4 Hz, 1H); 7.22-7.19 (m, 1H); 7.07-7.04 (m, 1H); 6.24 (d, J=1.2 Hz, 1H); 5.00 (m, 1H); 4.49-4.38 (m, 2H); 3.62-3.54 (m, 2H); 3.48-3.40 (m, 2H); 3.38 (s, 2H); 3.10 (s, 3H); 2.97-2.87 (m, 2H); 2.79-2.71 (m, 2H); 2.62-2.57 (m, 2H); 2.06-2.00 (m, 1H); 1.60 (m, 3H); 0.88 (m, 4H).

MS (ESI, m/z): 662.02 [M+H$^+$] for $C_{29}H_{32}N_3O_{11}PS$; $t_R$=0.67 min.

Example 4: ((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate Starting from the compound of Preparation D (0.2 g; 0.46 mmol) and the compound of Preparation F (0.222 g; 0.6 mmol) and proceeding in analogy to Procedure D (67% yield) and Procedure C (24% yield), the title compound was obtained as a beige solid (0.034 g).

$^1$H NMR (d6-DMSO) δ: 10.94 (br. s, 1H); 9.18 (br. s, 1H); 7.53 (d, J=0.9 Hz, 1H); 6.23 (d, J=1.2 Hz, 1H); 4.42 (s, 2H); 3.77 (m, 1H); 3.61 (m, 1H); 3.53-3.43 (overlapped m, 2H); 3.05 (s, 3H); 2.58 (m, 1H); 1.96 (m, 1H); 1.58-1.53 (m, 2H); 1.52 (s, 3H); 0.99 (m, 1H); 0.93 (m, 1H).

MS (ESI, m/z): 514.01 [M+H$^+$] for $C_{20}H_{24}N_3O_9PS$; $t_R$=0.55 min.

Example 5: ((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate Starting from the compound of Preparation D (0.5 g; 1.18 mmol) and intermediate F.i (0.3 g; 1.71 mmol) and proceeding in analogy to Procedure D (86% yield), Example 1, step 1.i (using as coupling partner the compound of Preparation E; 52% yield) and Procedure C (53% yield), the title compound was obtained as a yellowish solid (0.183 g).

$^1$H NMR (d6-DMSO) δ: 10.93 (br. s, 1H); 9.18 (br. s, 1H); 7.55 (s, 1H); 7.27 (m, 1H); 7.23 (m, 1H); 7.18 (m, 1H); 7.00 (m, 1H); 6.24 (d, J=1.2 Hz, 1H); 4.42 (s, 2H); 3.97 (m, 1H); 3.86 (m, 1H); 3.52-3.42 (overlapped m, 2H); 3.05 (s, 3H); 2.88 (t, J=7.6 Hz, 2H); 2.66-2.50 (overlapped m, 3H); 1.95 (m, 1H); 1.59 (m, 1H); 1.54 (m, 1H); 1.52 (s, 3H); 1.00 (m, 1H); 0.93 (m, 1H).

MS (ESI, m/z): 662.01 [M+H$^+$] for $C_{29}H_{32}N_3O_{11}PS$; $t_R$=0.63 min.

Example 6: ((1R,2R)-1-fluoro-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate Starting from the compound of Preparation D (0.2 g; 0.46 mmol) and the compound of Preparation G (0.250 g; 0.65 mmol) and proceeding in analogy to Procedure D (74% yield) and Procedure C (63% yield), the title compound was obtained, after purification by prep-HPLC (Method 3), as a beige solid (0.106 g).

$^1$H NMR (d6-DMSO) δ: 10.94 (br. s, 1H), 9.18 (br. s, 1H); 7.57 (d, J=0.6 Hz, 1H); 6.26 (d, J=1.2 Hz, 1H); 4.42 (s, 2H); 3.98-4.17 (m, 2H); 3.47 (m, 1H); 3.39 (overlapped m, 1H); 3.06 (s, 3H); 2.58 (m, 1H); 2.10 (m, 1H); 1.96 (m, 1H); 1.52 (s, 3H); 1.40-1.50 (m, 2H).

MS (ESI, m/z): 531.95 [M+H$^+$] for $C_{20}H_{23}N_3O_9FPS$; $t_R$=0.54 min.

Example 7: mono-ammonium (R)-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy)phosphonate 7.i. Tert-butyl hydrogen (((R)-4-(6-((1-(((tert-butyldiphenylsilyl)oxy)methyl)cyclopropyl)buta-, 3-diyn-1-yl)-3-oxo-1H-pyrrolo[1,2-c]imidazol-2(3H)-yl)-2-methyl-2-(methylsulfonyl)butanamido)oxy)phosphonate To a solution of intermediate 3.i (0.830 g, 1.24 mmol) in DCM (12 mL) was added tetrazole (0.45M in MeCN, 8.26 mL; 3.71 mmol) at 0° C. and di-tert-butyl diisopropylphosphoramidite (0.615 mL; 1.85 mmol). The solution was stirred at 0° C. for 20 min. The reaction was cooled down to −50° C. and MCPBA (0.283 g; 1.26 mmol) was added. The reaction was stirred at 0° C. for 1 h. 10% aq. NaHSO$_3$ (1 mL) was added, followed by water (10 mL). The two layers were separated and the aq. layer was extracted with DCM (10 mL). The evaporation residue was purified by CC (Hept-EA-MeOH) to afford the title compound as a yellowish solid (0.109 g; 11% yield).

MS (ESI, m/z): 752.07 [M-tBu+H$^+$] for $C_{40}H_{50}N_3O_9PSSi$; $t_R$=1.04 min.

7.ii. Mono-ammonium (R)-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy)phosphonate Starting from intermediate 7.i (0.1 g; 0.12 mmol) and proceeding in analogy to Reference Example 1, step RE1.ii (47% yield) and Procedure D (8% yield), the title compound was obtained, after purification by prep-HPLC (Method 1), as a white solid (0.445 g).

$^1$H NMR (d6-DMSO) δ: 7.54 (s, 1H); 6.23 (d, J=1.2 Hz, 1H); 4.47 (m, 2H); 3.63-3.54 (overlapped m, 1H); 3.44-3.39 (overlapped m, 1H); 3.39-3.36 (m, 2H); 3.11 (s, 3H); 2.50 (overlapped m, 1H); 2.05-1.95 (m, 1H); 1.53 (s, 3H); 0.97-0.82 (m, 4H).

MS (ESI, m/z): 513.99 [M+H$^+$] for $C_{20}H_{27}N_4O_9PS$; $t_R$=0.57 min.

Example 8: (R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl hydrogen sulfate To a solution of intermediate RE1.ii (0.1 g; 0.149 mmol) in Pyr (0.66 mL) was added Pyr.SO$_3$ complex (0.105 g; 0.298 mmol). The reaction mixture was stirred for 3 h. 4M aq. HCl (0.2 mL) was added and the mixture was purified by prep-HPLC (Method 2) to afford the title compound as a brown solid (0.005 g; 5% yield).

MS (ESI, m/z): 598.02 [M+H$^+$] for $C_{25}H_{31}N_3O_{10}S_2$; $t_R$=0.66 min.

Pharmacological Properties of the Invention Compounds

In Vitro Assays

Bacterial Growth Minimal Inhibitory Concentrations:

Experimental Methods:

Minimal Inhibitory Concentrations (MICs; mg/L) were determined in cation-adjusted Mueller-Hinton Broth by a microdilution method following the description given in "*Methods for Dilution Antimicrobial Susceptibility Tests for Bacteria that Grow Aerobically*", Approved standard, 7$^{th}$ ed., Clinical and Laboratory Standards Institute (CLSI) Document M7-A7, Wayne, Pa., USA (2006).

Results:

All Reference Example compounds were tested against against several Gram-negative bacteria. *K. pneumoniae* A-651 is a multiply resistant strain (in particular quinolone-resistant), while *E. coli* ATCC25922, wild-type *E. coli* A-1261 and *P. aeruginosa* ATCC27853 are quinolone-sensitive strains. The corresponding antibacterial test results are given in Table 1 hereafter (MICs in mg/L).

TABLE 1

| Example No. | MIC for *E. coli* ATCC25922 | MIC for *E. coli* A-1261 | MIC for *P. aeruginosa* ATCC27853 | MIC for *K. Pneumoniae* A-651 |
| --- | --- | --- | --- | --- |
| RE1 | 0.5 | 0.25 | 1 | 1 |
| RE2 | 0.25 | 0.125 | 0.25 | 0.25 |
| RE3 | 0.25 | 0.25 | 0.5 | 0.5 |
| Cipro | ≤0.063 | ≤0.063 | 0.125 | >8 |

All Example compounds were tested against against wild-type *E. coli* A-1261 in the absence of alkaline phosphatase or esterase, in the presence of an alkaline phosphatase and in the presence of an esterase. The corresponding antibacterial test results are given in Table 2 hereafter (MICs in mg/L).

TABLE 2

| | | MIC for *E. coli* A-1261 | | |
| --- | --- | --- | --- | --- |
| Example No. | Active Metabolite Reference Example No. | In the absence of alkaline phosphatase or esterase | In the presence of an alkaline phosphatase (2 i.U./mL) | In the presence of an esterase (10 i.U./mL) |
| 1 | RE1 | 2 | 1 | 0.25 |
| 2 | RE1 | 8 | 1 | 1 |
| 3 | RE1 | 8 | 0.5 | 8 |
| 4 | RE2 | >8 | 0.25 | >8 |
| 5 | RE2 | 4 | 0.25 | 0.25 |
| 6 | RE3 | >8 | 0.5 | >8 |
| 7 | RE1 | 4 | 1 | 4 |
| 8 | RE1 | 2 | 2 | 2 |

The invention claimed is:

1. A compound of formula I

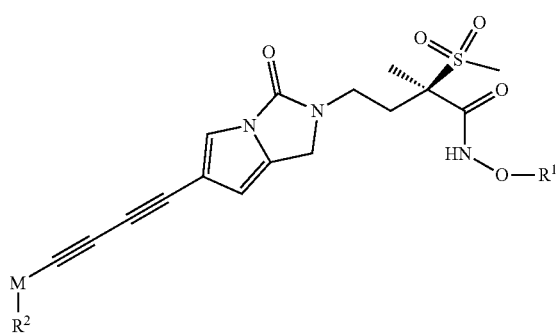

wherein

M is one of the groups $M^A$, $M^B$ and $M^C$ represented below

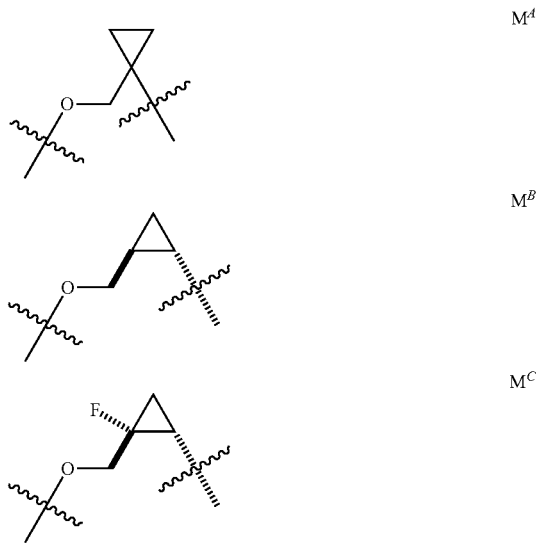

and either $R^1$ represents H and, when M is $M^A$, $R^2$ represents SO$_3$H, phosphonooxymethyl or the group $L^{2A}$ represented below

wherein $R^{2A}$ represents (C$_1$-C$_4$)alkylamino(C$_1$-C$_4$)alkyl, [di (C$_2$-C$_4$)alkylamino]methyl, {(methyl)[(C$_{2-4}$)alkyl]amino}methyl, [di(C$_1$-C$_4$)alkylamino](C$_2$-C$_4$)alkyl, morpholin-4-yl-(C$_1$-C$_4$)alkyl, phosphonooxy(C$_1$-C$_4$)alkyl, phosphonooxymethoxy, 2-(phosphonooxy-(C$_1$-C$_4$)alkyl)-phenyl, (2-(phosphonooxy)-phenyl)-(C$_1$-C$_4$)alkyl or [2-(phosphonooxy-(C$_1$-C$_4$)alkyl)-phenyl]-(C$_1$-C$_4$)alkyl, or, when M is $M^B$ or $M^C$, $R^2$ represents PO$_3$H$_2$, SO$_3$H, phosphonooxymethyl or the group $L^{2BC}$ represented below

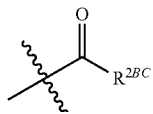
L$^{2BC}$ wherein R$^{2BC}$ represents (C$_1$-C$_4$)alkylamino(C$_1$-C$_4$)alkyl, [di(C$_1$-C$_4$)alkylamino](C$_1$-C$_4$)alkyl, morpholin-4-yl-(C$_1$-C$_4$)alkyl, phosphonooxy(C$_1$-C$_4$)alkyl, phosphonooxymethoxy, 2-(phosphonooxy-(C$_1$-C$_4$)alkyl)-phenyl, (2-(phosphonooxy)-phenyl)-(C$_1$-C$_4$)alkyl or [2-(phosphonooxy-(C$_1$-C$_4$)alkyl)-phenyl]-(C$_1$-C$_4$)alkyl, or R$^2$ represents H and R$^1$ represents PO$_3$H$_2$, SO$_3$H, phosphonooxymethyl or the group L$^1$ represented below

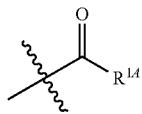
L$^1$ wherein R$^{1A}$ represents (C$_1$-C$_4$)alkylamino(C$_1$-C$_4$)alkyl, [di(C$_1$-C$_4$)alkylamino](C$_1$-C$_4$)alkyl, morpholin-4-yl-(C$_1$-C$_4$)alkyl, phosphonooxy(C$_1$-C$_4$)alkyl, phosphonooxymethoxy, 2-(phosphonooxy-(C$_1$-C$_4$)alkyl)-phenyl, (2-(phosphonooxy)-phenyl)-(C$_1$-C$_4$)alkyl or [2-(phosphonooxy-(C$_1$-C$_4$)alkyl)-phenyl]-(C$_1$-C$_4$)alkyl;

it being understood that the molecule is always such that its R$^2$ group is attached to the oxygen atom of its M$^A$, M$^B$ and M$^C$ group;
or a salt thereof.

2. The compound of formula I according to claim 1, wherein the compound is a compound of formula I$_{CE}$

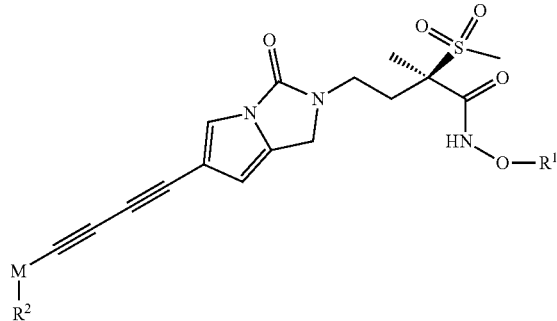
I$_{CE}$ wherein
M is one of M$^A$, M$^B$ or M$^C$ represented below

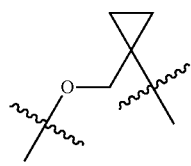
M$^A$

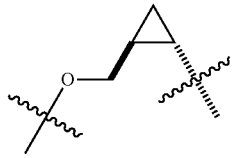
M$^B$

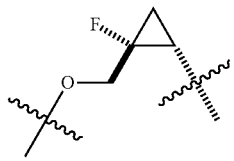
M$^C$ and either R$^1$ represents H and, when M is M$^A$, R$^2$ represents SO$_3$H or the group L$^{2A}$ represented below

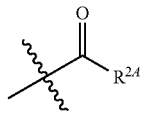
L$^{2A}$ wherein, R$^{2A}$ represents morpholin-4-yl-(C$_1$-C$_4$)alkyl or (2-(phosphonooxy)-phenyl)-(C$_1$-C$_4$)alkyl, or, when M is M$^B$ or M$^C$, R$^2$ represents PO$_3$H$_2$ or the group L$^{2BC}$ represented below

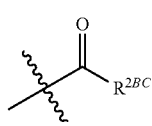
L$^{2BC}$ wherein, R$^{2BC}$ represents (2-(phosphonooxy)-phenyl)-(C$_1$-C$_4$)alkyl,
or R$^2$ represents H and R$^1$ represents PO$_3$H$_2$ or the group L$^1$ represented below

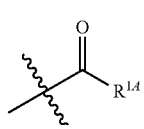
L$^1$ wherein R$^{1A}$ represents (2-(phosphonooxy)-phenyl)-(C$_1$-C$_4$)alkyl;
it being understood that the molecule is always such that its R$^2$ group is attached to the oxygen atom of its M$^A$, M$^B$ and M$^C$ group;
or a salt thereof.

3. The compound of formula I according to claim 1, wherein M is the group M$^A$;
or a salt thereof.

4. The compound of formula I according to claim 3, wherein R$^1$ represents H and R$^2$ represents SO$_3$H or the group L$^{2A}$ wherein R$^{2A}$ represents morpholin-4-yl-(C$_1$-C$_4$)alkyl or (2-(phosphonooxy)-phenyl)-(C$_1$-C$_4$)alkyl;
or a salt thereof.

5. The compound of formula I according to claim 3, wherein $R^2$ represents H and $R^1$ represents $PO_3H_2$ or the group $L^1$ wherein $R^{1A}$ represents 2-(2-(phosphonooxy)phenyl)ethyl;
or a salt thereof.

6. The compound of formula I according to claim 1, wherein M is the group $M^B$;
or a salt thereof.

7. The compound of formula I according to claim 6, wherein $R^1$ represents H and $R^2$ represents $PO_3H_2$ or the group $L^{2BC}$ wherein $R^{2BC}$ represents 2-(2-(phosphonooxy)phenyl)ethyl;
or a salt thereof.

8. The compound of formula I according to claim 1, wherein M is the group $M^C$;
or a salt thereof.

9. The compound of formula I according to claim 8, wherein $R^1$ represents H and $R^2$ represents $PO_3H_2$;
or a salt thereof.

10. The compound of formula I according to claim 1, wherein:
M is the group $M^A$, $R^1$ represents H and $R^2$ represents $SO_3H$ or the group $L^{2A}$ wherein $R^{2A}$ represents morpholin-4-yl-($C_1$-$C_4$)alkyl or (2-(phosphonooxy)-phenyl)-($C_1$-$C_4$)alkyl; or
M is the group $M^A$, $R^2$ represents H and $R^1$ represents $PO_3H_2$ or the group $L^1$ wherein $R^{1A}$ represents (2-(phosphonooxy)-phenyl)-($C_1$-$C_4$)alkyl; or
M is the group $M^B$, $R^1$ represents H and $R^2$ represents $PO_3H_2$ or the group $L^{2BC}$ wherein $R^{2BC}$ represents (2-(phosphonooxy)-phenyl)-($C_1$-$C_4$)alkyl; or
M is the group $M^C$, $R^1$ represents H and $R^2$ represents $PO_3H_2$;
or a salt thereof.

11. The compound of formula I according to claim 1, wherein the compound is:
(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 2-morpholinoacetate;
(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate;
(R)-2-(3-((4-(6-((1-(hydroxymethyl)cyclopropyl)buta-1,3-diyn-1-yl)-3-oxo-1H-pyrrolo[1,2-c]imidazol-2 (3H)-yl)-2-methyl-2-(methylsulfonyl)butanamido)oxy)-3-oxopropyl)phenyl dihydrogen phosphate;
-((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;
((1S,2S)-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl 3-(2-(phosphonooxy)phenyl)propanoate;
((1R,2R)-1-fluoro-2-((2-((R)-4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl dihydrogen phosphate;
(R)-((4-(6-((1-(hydroxymethyl)cyclopropyl)buta-1,3-diyn-1-yl)-3-oxo-1H-pyrrolo[1,2-c]imidazol-2(3H)-yl)-2-methyl-2-(methylsulfonyl)butanamido)oxy) phosphonic acid;
(R)-(1-((2-(4-(hydroxyamino)-3-methyl-3-(methylsulfonyl)-4-oxobutyl)-3-oxo-2,3-dihydro-1H-pyrrolo[1,2-c]imidazol-6-yl)buta-1,3-diyn-1-yl)cyclopropyl)methyl hydrogen sulfate;
or a salt thereof.

12. A method of treating a bacterial infection comprising administering to a patient in need thereof the compound of formula I according to claim 1, or a pharmaceutically acceptable salt thereof.

13. A pharmaceutical composition comprising, as active principle, a compound of formula I according to claim 1, or a pharmaceutically acceptable salt thereof, and at least one therapeutically inert excipient.

14. A method of treating a bacterial infection comprising administering to a patient in need thereof the pharmaceutical composition according to claim 13, or a pharmaceutically acceptable salt thereof.

15. The method according to claim 14, wherein the bacterial infection is a Gram-negative bacterial infection.

16. The method according to claim 13, wherein the bacterial infection is a Gram-negative bacterial infection.

* * * * *